US011863355B1

(12) United States Patent
Patil et al.

(10) Patent No.: US 11,863,355 B1
(45) Date of Patent: Jan. 2, 2024

(54) FAIL-SAFE CIRCUIT FOR A LOW VOLTAGE DIFFERENTIAL SIGNALING RECEIVER

(71) Applicant: Aronix LLC, Peachtree Corners, GA (US)

(72) Inventors: Arun Narayan Patil, Winder, GA (US); Anand Raghunath Bhave, Pune (IN); Varun Kaushik, Matsue (JP); Harshita Kaushik, Pune (IN)

(73) Assignee: Aronix LLC, Peachtree Corners, GA (US)

( * ) Notice: Subject to any disclaimer, the term of this patent is extended or adjusted under 35 U.S.C. 154(b) by 0 days.

(21) Appl. No.: 18/111,519

(22) Filed: Feb. 17, 2023

Related U.S. Application Data

(63) Continuation-in-part of application No. 18/074,222, filed on Dec. 2, 2022.

(51) Int. Cl.
*H04L 25/02* (2006.01)
*A61B 5/024* (2006.01)
*H03K 19/007* (2006.01)

(52) U.S. Cl.
CPC ...... *H04L 25/0272* (2013.01); *A61B 5/02411* (2013.01); *H03K 19/007* (2013.01); *A61B 5/02438* (2013.01)

(58) Field of Classification Search
CPC ............. H04L 25/0272; A61B 5/02411; A61B 5/02438; H03K 19/007
See application file for complete search history.

(56) References Cited

U.S. PATENT DOCUMENTS

| | | | | |
|---|---|---|---|---|
| 5,528,168 A | * | 6/1996 | Kleveland | H04L 25/0292 326/86 |
| 6,288,577 B1 | * | 9/2001 | Wong | H03K 5/24 326/14 |
| 6,320,406 B1 | * | 11/2001 | Morgan | H04L 25/08 326/14 |
| 6,650,149 B1 | * | 11/2003 | Wong | H03K 19/007 327/14 |
| 8,696,578 B2 | * | 4/2014 | Kabakov | A61B 8/40 600/453 |
| 2004/0090265 A1 | * | 5/2004 | Pradhan | H03F 3/68 330/69 |
| 2010/0168596 A1 | * | 7/2010 | Jaeschke | A61B 8/5276 600/511 |
| 2010/0274145 A1 | * | 10/2010 | Tupin, Jr. | A61B 5/0022 600/511 |
| 2013/0123637 A1 | * | 5/2013 | Wohlschlager | A61B 8/02 600/453 |

(Continued)

Primary Examiner — Sanjay Cattungal
(74) Attorney, Agent, or Firm — H. Brock Kolls

(57) ABSTRACT

The present invention relates to differential receivers, and more particularly to a fail-safe circuit for low-voltage differential signaling (LVDS) receivers having single differential input disconnect detection with a latchable control signal interrupt capability. In operation, the receiver output is applied to a Vout output as long as the control signal is in a normal operating state, and on the first occurrence of a fault condition trigger is applied to the input of a latch, the latch latches applying a fault state to the control signal which causes the Vout output to follow the control signal blocking the receiver output until the latch is reset after the fault has been corrected.

21 Claims, 11 Drawing Sheets

(56) References Cited

U.S. PATENT DOCUMENTS

| | | | |
|---|---|---|---|
| 2013/0158407 A1* | 6/2013 | Kabakov | A61B 8/0866 600/453 |
| 2013/0245436 A1* | 9/2013 | Tupin, Jr. | A61B 5/6833 600/430 |
| 2014/0276070 A1* | 9/2014 | Kabakov | A61B 8/0883 600/453 |
| 2015/0146772 A1* | 5/2015 | Fujimori | H04B 1/12 375/238 |

* cited by examiner

FAIL-SAFE CIRCUIT FOR A LOW VOLTAGE DIFFERENTIAL SIGNALING RECEIVER

CROSS-REFERENCE TO RELATED APPLICATIONS

This application contains subject matter which is related to the subject matter of the following co-pending application. The below-listed application is hereby incorporated herein by reference in its entirety:
  This is a U.S. non-provisional application that is a continuation in part of a U.S. non-provisional application Ser. No. 18/074,222, inventor Arun Narayan Patil et al., entitled "FETAL HEART RATE TRANSDUCER", filed Dec. 2, 2022.

TECHNICAL FIELD OF THE INVENTION

The present invention relates to differential receivers, and more particularly to a fail-safe circuit for low-voltage differential signaling (LVDS) receivers having single differential input disconnect detection with a latchable control signal interrupt capability.

BACKGROUND OF THE INVENTION

Before our invention, it was common for transmitting and receiving devices to be interconnected by a cable. While there can be many electrical configuration options for communicating signals and data using a pair of wires between devices over a distance, one such technique utilizes a low voltage differential signal (LVDS) scheme. In this type of configuration, a receiver output varies based on a pair of input signals.

Alone prior LVDS circuits can produce erroneous results in a fault condition when one or both input wires are shorted or disconnected. To mitigate some of these fault conditions a frontend circuit to the LVDS comprises a pull-up resistor on each input line and a termination resistor between the input lines. The frontend circuit is intended to address faults where one or both input lines are disconnected by providing a known state is such conditions at the input to the LVDS.

The frontend (pull-up resistor bias) circuit however does not address certain other fault conditions of an out-of-range nature. In this regard, the prior LVDS circuit utilizes a backend (parallel) circuit that includes comparators, a single voltage reference, and logic gates to block the receiver output from the differential receiver when an out-of-range fault condition is detected such as both of the inputs are not driven from the transmitter (high impedance state) or both the inputs are open circuit, or both the inputs are shorted to each other. In this regard, prior fail-safe circuits only detect these three failure conditions as a de facto industry standard.

While prior LVDS circuits address certain fault conditions with frontend (pull-up resistor bias) and backend (parallel) circuits they don't address all of them. In this regard, a shortcoming of prior LVDS circuits is that when one of the input lines is disconnected (open circuit) the receiver output is not blocked. In certain applications, such as fetal heart rate monitors, it can cause the transducer that is placed on the pregnant mother and which is receiving a differential signal (reference clock) on the inputs from the fetal heart rate monitor, to send erroneous fetal heart rate data to the fetal heart rate monitor without even transmitting ultrasound beam or receiving ultrasound Doppler echo signal. The result can be that an incorrect exceedingly low or high fetal heart rate can be reported. Such a low or high fetal heart rate can be interpreted by medical professionals that the unborn baby is in a dangerous situation all because one of the input lines to the LVDS has become disconnected such as when a wire in the cable loosens or breaks.

Another shortcoming of prior LVDS circuits is on the first occurrence of a fault condition the receiver output isn't latched off preventing further output until the source of the fault condition is corrected and the LDVS circuit is reset. In this regard, when one of the inputs is disconnected or otherwise broken in an intermittent manner making and breaking the compromised connection such as when the patient moves or the cable wiggles, prior LVDS circuits fail to latch off stopping the operation. As a result, erroneous signal input conditions can create erroneous data outputs which can cause incorrect results to be displayed. Such incorrect results can lead to medical professionals and others making patient and unborn baby medical decisions based on incorrect fetal heart rate readings.

The present invention addresses these and other shortcomings by providing a fail-safe differential receiver having a single differential input disconnect detection capability with a latchable control signal and other advantages. For these reasons and shortcomings as well as other reasons and shortcomings there is a long-felt need that gives rise to the present invention.

SUMMARY OF THE INVENTION

The shortcomings of the prior art are overcome and additional advantages are provided through the provision of a fail-safe differential receiver having single differential input disconnect detection with a latchable control signal interrupt capability. The fail-safe differential receiver comprises a first voltage reference, a second voltage reference, and a differential amplifier. The differential amplifier comprises a receiver output and receives an IN+ input, and an IN− input. The fail-safe differential receiver comprises more than one comparator. Each of the comparators comprises a compared output and receives at least two of the following: the IN+ input, the IN− input, the first voltage reference, or the second voltage reference. A latch-capable combinational logic device receives each of the compared outputs, and the receiver output. The latch-capable combinational logic device comprises a latch, and a control signal that is switched to a normal operating state until at least one of the following is detected:
  when the IN+ input is open (not connected) the control signal is latched to the fault condition state;
  when the IN− input is open (not connected) the control signal is latched to the fault condition state;
  when the IN+ input and the IN− input are connected by a first resistance, that is configured as an undriven parallel termination, the control signal is latched to the fault condition state;
  when the IN+ input is shorted to Vcc or GND the control signal is latched to the fault condition state;
  when the IN− input is shorted to Vcc or GND the control signal is latched to the fault condition state;
  when the IN+ input and the IN− input are shorted together the control signal is latched to the fault condition state; and
  when only one of the IN+ input or the IN− input is intermittently open and reconnected the control signal is latched to the fault condition state;

In operation, the receiver output is applied to a Vout output as long as the control signal is in the normal operating state, and on the first occurrence of the fault condition state the latch latches blocking the receiver output from being applied to the Vout output until the latch is reset.

Additional shortcomings of the prior art are overcome and additional advantages are provided through the provision of a fail-safe differential receiver having single differential input disconnect detection with latchable control signal interrupt capability. The fail-safe differential receiver comprises a first voltage reference, a second voltage reference, and a differential amplifier. The differential amplifier comprises a receiver output and receives an IN+ input, and an IN− input. A first voltage follower operational amplifier comprises a first op-amp output and receives the receiver output. A rectifier peak detector comprises a peak output and receives the first op-amp output. A second voltage follower operational amplifier comprises a second op-amp output and receives the peak output. A window comparator comprises a window compared output and receives the second op-amp output, a first reference voltage, and a second reference voltage. A latch-capable combinational logic device receives the window compared output and the receiver output. The latch-capable combinational logic device comprises a latch and a control signal that is switched to a normal operating state until at least one of the following is detected:
 when the IN+ input is open (not connected) the control signal is latched to the fault condition state;
 when the IN− input is open (not connected) the control signal is latched to the fault condition state;
 when the IN+ input and the IN− input are connected by a first resistance, that is configured as an undriven parallel termination, the control signal is latched to the fault condition state;
 when the IN+ input is shorted to Vcc or GND the control signal is latched to the fault condition state;
 when the IN− input is shorted to Vcc or GND the control signal is latched to the fault condition state;
 when the IN+ input and the IN− input are shorted together the control signal is latched to the fault condition state; and
 when only one of the IN+ input or the IN− input is intermittently open and reconnected the control signal is latched to the fault condition state.

In operation, the receiver output is applied to a Vout output as long as the control signal is in the normal operating state, and on the first occurrence of the fault condition state the latch latches blocking the receiver output from being applied to the Vout output until the latch is reset.

Additional shortcomings of the prior art are overcome and additional advantages are provided through the provision of a fail-safe differential receiver having latchable control signal interrupt capability. The fail-safe differential receiver comprises a differential amplifier. The differential amplifier comprises a receiver output and receives an IN+ input, and an IN− input. A first combining gate receives the receiver output, a control signal, and generates a Vout output.

The fail-safe differential receiver further comprises a first reference voltage and a first comparator. The first comparator receives the IN+ input and the first reference voltage and generates a first compare signal. A second comparator receives the IN− input and the first reference voltage, and generates a second compare signal. A second combining gate receives the first compare signal and the second compare signal and generates a third compare signal.

The fail-safe differential receiver further comprises a second reference voltage and a third comparator. The third comparator receives the IN+ input and the second reference voltage and generates a fourth compare signal. A fourth comparator receives the IN− input and the second reference voltage and generates a fifth compare signal. A third combining gate receives the fourth compare signal and the fifth compare signal and generates a sixth compare signal. A fourth combining gate receives the third compare signal and the sixth compare signal and generates a seventh compare signal. And a latch receives the seventh compare signal and generates the control signal. The control signal transitions between a normal operating state and a fault condition state.

In operation, the receiver output is applied to a Vout output as long as the control signal is in the normal operating state, and on the first occurrence of the fault condition state the latch latches blocking the receiver output from being applied to the Vout output until the latch is reset.

Additional shortcomings of the prior art are overcome and additional advantages are provided through the provision of a method of using a fail-safe differential receiver having single differential input disconnect detection with latchable control signal interrupt capability. The method comprises the step of connecting a device that comprises a fail-safe differential receiver to a signal-transmitting device by way of a communication line. The communication line comprises a plurality of electrical connections that include an IN+ input, an IN−, Vcc, and ground (GND). The fail-safe differential receiver is configured in one of the following ways:
 either the fail-safe differential receiver comprises a first voltage reference, a second voltage reference, and a differential amplifier. The differential amplifier comprises a receiver output and receives the IN+ input, and the IN− input. The fail-safe differential receiver comprises more than one comparator. Each of the comparators comprises a compared output and receives at least two of the following: the IN+ input, the IN− input, the first voltage reference, or the second voltage reference. And a latch-capable combinational logic device receives each of the compared output, and the receiver output. The latch-capable combinational logic device comprises a latch, and a control signal.
 Or, the fail-safe differential receiver comprises the first voltage reference, the second voltage reference, and the differential amplifier. The differential amplifier comprises the receiver output and receives the IN+ input, and the IN− input. A first voltage follower operational amplifier comprises a first op-amp output and receives the receiver output. A rectifier peak detector comprises a peak output and receives the first op-amp output. A second voltage follower operational amplifier comprises a second op-amp output and receives the peak output. A window comparator comprises a window compared output and receives the second op-amp output, a first reference voltage, and a second reference voltage. The latch-capable combinational logic device receives the window compared output and the receiver output. The latch-capable combinational logic device comprises a latch, and the control signal.

The method continues by transitioning the control signal based on inputs to the latch-capable combinational logic device, the control signal is switched to a normal operating state until at least one of the following is detected:
 when the IN+ input is open (not connected) the control signal is latched to the fault condition state;
 when the IN− input is open (not connected) the control signal is latched to the fault condition state;
 when the IN+ input and the IN− input are connected by a first resistance, that is configured as an undriven parallel termination, the control signal is latched to the fault condition state;

when the IN+ input is shorted to Vcc or GND the control signal is latched to the fault condition state;

when the IN− input is shorted to Vcc or GND the control signal is latched to the fault condition state;

when the IN+ input and the IN− input are shorted together the control signal is latched to the fault condition state; and when only one of the IN+ input or the IN− input is intermittently open and reconnected the control signal is latched to the fault condition state;

In operation, the receiver output is applied to a Vout output as long as the control signal is in the normal operating state, and on first occurrence of the fault condition state the latch latches blocking the receiver output from being applied to the Vout output until the latch is reset.

System and computer program products corresponding to the above-summarized methods are also described and claimed herein.

Additional features and advantages are realized through the techniques of the present invention. Other embodiments and aspects of the invention are described in detail herein and are considered a part of the claimed invention. For a better understanding of the invention with advantages and features, refer to the description and the drawings.

BRIEF DESCRIPTION OF THE FIGURES

The subject matter which is regarded as the invention is particularly pointed out and distinctly claimed in the claims at the conclusion of the specification. The foregoing and other objects, features, and advantages of the invention are apparent from the following detailed description taken in conjunction with the accompanying drawings in which:

The detailed description explains the preferred embodiments of the invention, together with advantages and features, by way of example with reference to the drawings.

DETAILED DESCRIPTION OF THE INVENTION

Electronic systems such as networking equipment often transmit signals over cables. Although the cables may be only a few meters in length, a transmission-line effect degrades data quality and transmission rate. Large signal swings can also increase electromagnetic interference (EMI) and system noise. To send signals over these cables reliably often requires special line drivers and receivers.

Attempts to mitigate issues related to signal transmission reliability by techniques such as reduced voltage swings, and utilizing a pair of physical signals driven to opposite states used together to transmit a single logical signal. Such differential signaling has been used with Emitter-coupled logic (ECL) for many years and in low-voltage differential signaling (LVDS) drivers and receivers.

In operation, LVDS drivers have a pair of outputs that are driven to opposite states. The two outputs are sent separately down the cable to the LVDS receiver. At the far (receiver) end of the cable, the lines are connected by a terminating resistor. A current loop exists from one transmitter output, down the cable, through the terminating resistor, and back through the cable to the other transmitter line output. A voltage drop occurs across the terminating resistor that is sensed by the receiver. However, the voltage difference across the terminating resistor between the two signals is small, perhaps only a few hundred millivolts. Sensitive receivers are needed to detect such a small voltage difference between the two signal lines.

In real-life systems, cables can become disconnected, such as by a system/network technician when networks are modified, or when a cable fails due to continuous flexing operation. The transmitter can also fail or be in a high-impedance output state. At these times, neither output line is driven, and the voltage across the terminating resistor drops to near zero. Noise can be coupled into the cable from various sources, and this noise can be picked up by the receiver's differential inputs and amplified. The output of the receiver can oscillate as the noise is amplified, and false triggering of receiver logic can occur. In short, spurious noise can cause reading/signal processing errors.

The present invention relates to differential receivers, and more particularly to a fail-safe circuit for low-voltage differential signaling (LVDS) receivers having single differential input disconnect detection with a latchable control signal interrupt capability.

Figure 1:
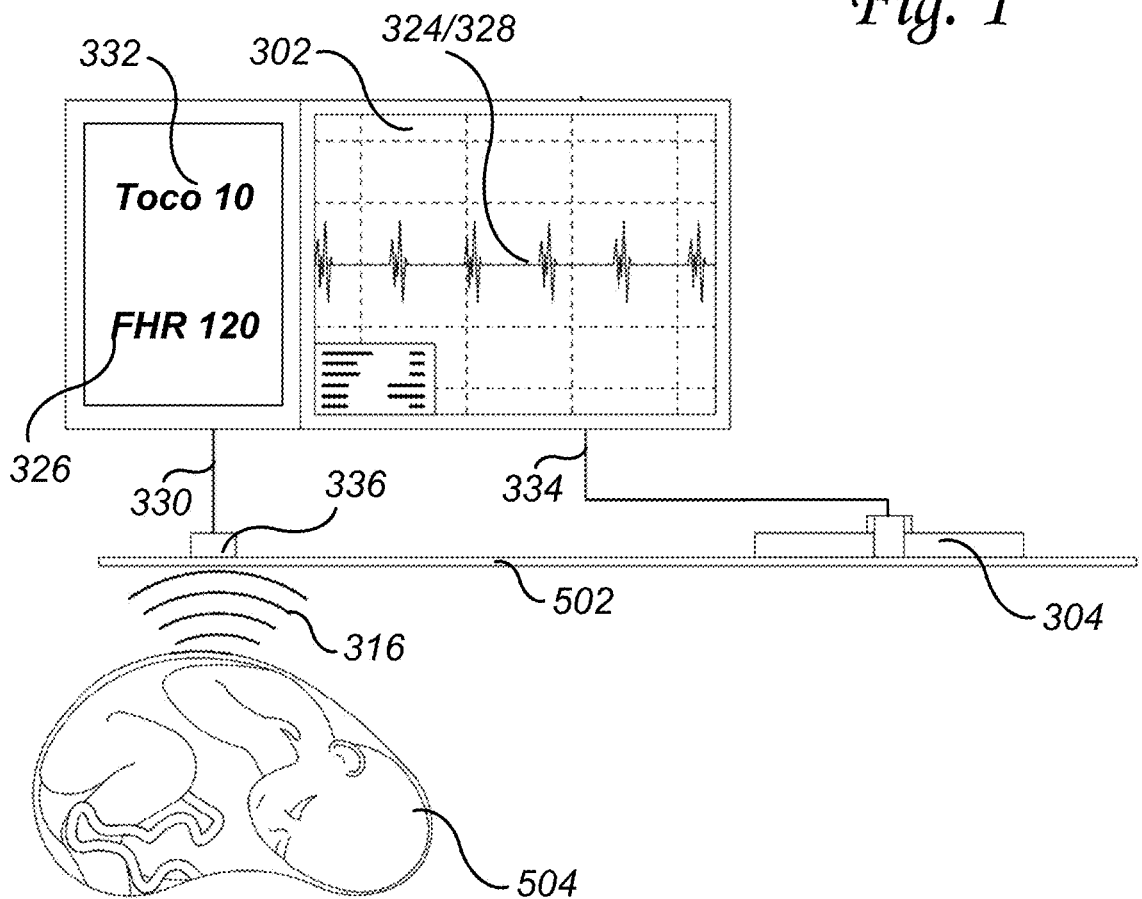
FIG. 1 illustrates one example of a device that comprises a fail-safe differential receiver having single differential input disconnect detection with a latchable control signal interrupt capability configured for use in a fetal heart rate monitor application.
Figure 1:
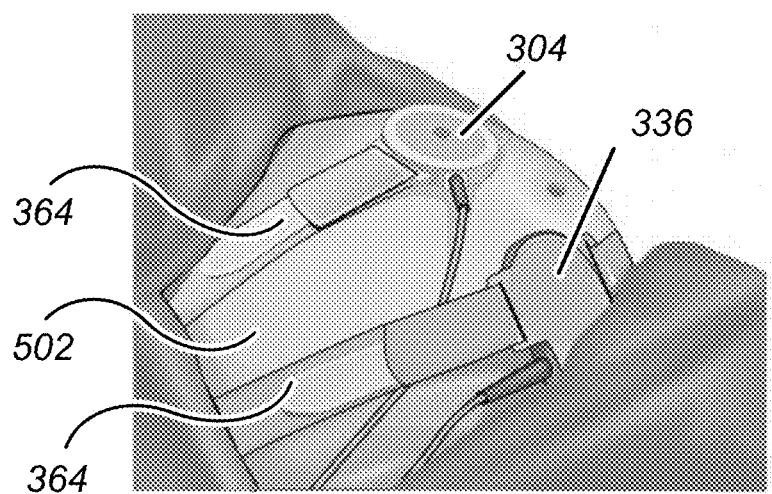

Turning now to the drawings in greater detail, it will be seen that in FIG. 1 there is illustrated one example of a device that comprises a fail-safe differential receiver having single differential input disconnect detection with a latchable control signal interrupt capability configured for use in a fetal heart rate (FHR) monitor application. In an exemplary embodiment, an FHR transducer 336 can be secured with a belt 364 to the lower abdomen of a pregnant patient 502. Additionally, a Toco transducer 304 to measure contractions can be secured by a belt 364 to the patient and interconnect by way of a cable 334 with the FHR monitor 302 to display a Toco count 332 and associated waveform 328.

The FHR transducer 336 is interconnected by way of a cable 330 with the FHR monitor 302. The FHR monitor 302 provides a waveform that is received at the FHR transducer 336 by way of the fail-safe differential receiver 100. The waveform is used to operate a plurality of ultrasound PZT (Lead Zirconate Titanate) discs, within the FHR transducer 336, broadcast the waveform by way of ultrasound, and receive a return ultrasound Doppler echo signal 316 related to the heartbeat rate of the unborn baby. The return ultrasound Doppler echo signal is processed, communicated back to the FHR monitor 302, and displayed 326/324 on the FHR monitor 302 as the fetus heart rate (FHR) waveform.

The FHR transducer 336 can be a Philips Fetal Ultrasound Transducer models M1356A, 15245A, Avalon M2736A, M2736AA, Ref #867246, Avalon CTS M2726A, Avalon CL Ref #866076, GE Corometrics Nautilus ultrasound models 5700AAX, 5700BAX, 5700LAX, 5700HAX, REF #2108346-001, or other suitable FHR transducers. A shortcoming in each of these FHR transducers 336 is that they lack a fail-safe differential receiver having single differential input disconnect detection with a latchable control signal interrupt capability as taught in the present invention. This means that the prior FHR transducers 336 that use a prior LVDS cannot detect the first occurrence of a cable signal fault and latch the signal off to prevent erroneous FHR readings 326 generated by spurious noise from being processed and displayed on the FHR monitor 302. In short, prior LVDS cannot, upon the first detection occurrence of an intermittent or permanent cable 330 fault, trigger a latch that blocks the signal disabling the FHR transducer 336 until the source of the fault is corrected and the LVDS is reset.

In this regard, the Philips Avalon ultrasound transducer models M2736A, M2736AA, and Ref #867246 employ an LVDS line receiver (Maxim/Analog Devices MAX9111/MAX9130) to extract the 1 MHz reference clock from a differential signal received from the fetal monitor (FM20/30/40/50) over a 7-conductor shielded cable 330 with 2.2V common mode direct current (DC) voltage bias. These LVDS receiver IC chips have a fail-safe detection circuit that blocks the output when three distinct fault conditions occur—(1) both the inputs are open, (2) both the inputs are shorted together and (3) both the inputs are un-driven while a termination resistor is intact at the receiver input/the LVDS transmitter output (at fetal monitor 302) is in a high impedance state (electrically floating).

A shortcoming of the prior LVDS line receivers is that if only one of the inputs is open (unconnected), the fail-safe detection circuit does not block the LVDS output, and hence random spurious noise from the LVDS receiver's floating input is allowed to pass to the processing circuit 408, which in turn, results in spurious and inaccurate fetal heart rate determinations and display 326/324 on the FHR monitor 302.

Exacerbating this shortcoming is that before a cable 330 fails completely (open-circuited permanently), one or more of the cable 330 signal conductors can intermittently break continuity while the cable 330 flexes and spurious/wrong fetal heart rate readings 326/324 can lead to mistaken clinical interpretation by medical professionals.

Figure 2:
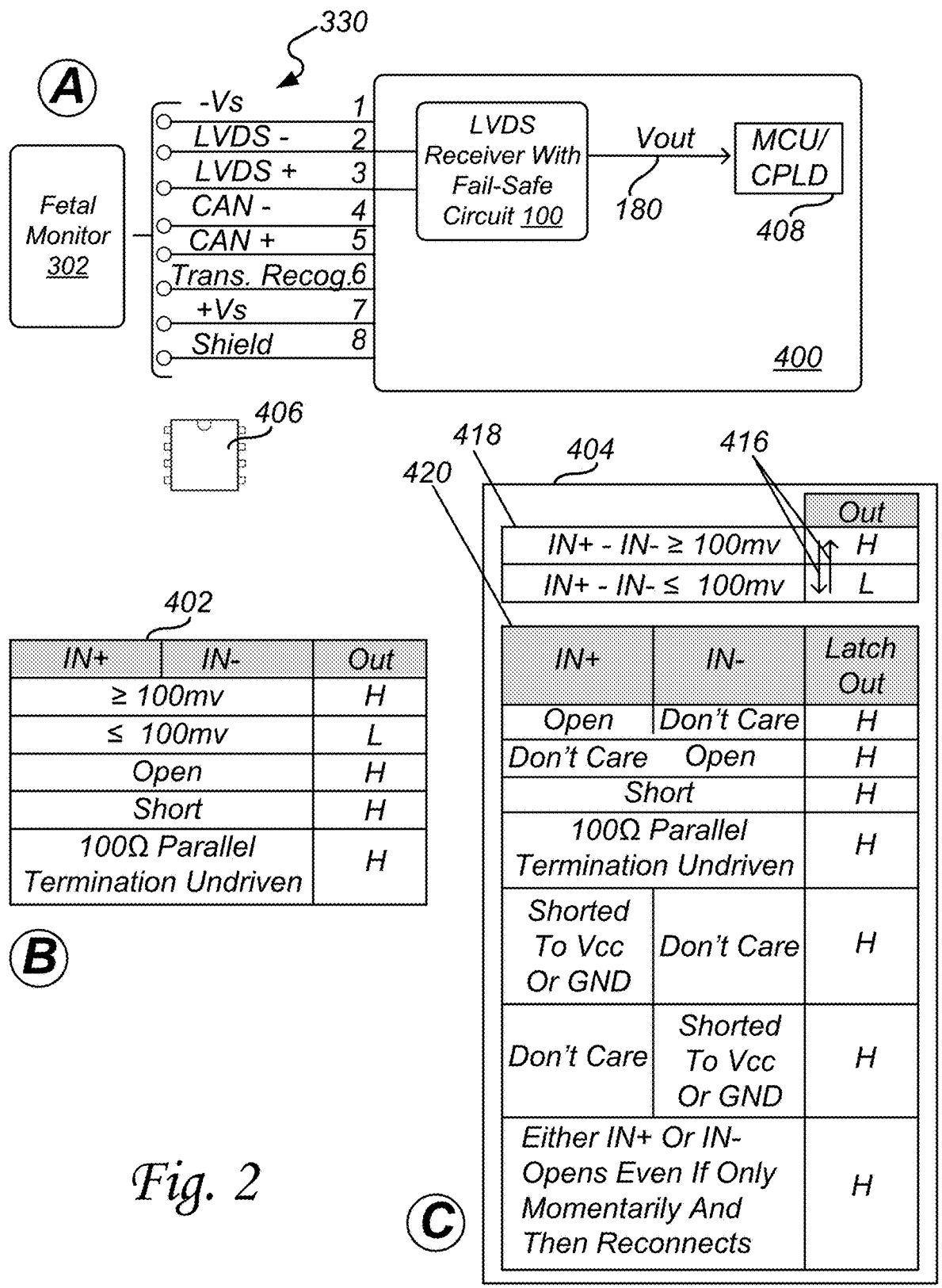
FIG. 2 illustrates one example of a logic state table for a fail-safe differential receiver having single differential input disconnect detection with a latchable control signal interrupt capability.

Referring to FIG. 2, there is illustrated one example of a logic state table for a fail-safe differential receiver 100 having single differential input disconnect detection with latchable control signal interrupt capability. Reference 'A' illustrates the seven-conductor (plus the shield) cable 330 illustrated in at least FIG. 8, if any of the five conductors on pins 1, 4, 5, 6, or 7, breaks (electrically open) then the transducer completely stops working but if one of the remaining two conductor connector pins 2 or 3 (LVDS+/−) breaks (electrically open) then the transducer becomes noisy and gives spurious FHR readings even though there is no ultrasound beam transmission from the transducer and hence no return ultrasound Doppler echo signal to be processed. These two conductors (pins 2 and 3) carry a 1 MHz reference clock signal from the fetal monitor to the transducer head that is processed through the LVDS receiver chip on the backend PCB (signal processor 408). In an exemplary embodiment, pin 1 is −Vs, pin 2 is LVDS-connected to IN− 129, pin 3 is LVDS+ connected to IN+ 127, pin 4 is controller area network (CAN) Bus−, pin 5 is CAN Bus+, pin 6 is Transducer Recognition, pin 7 is +Vs, and cable shield is connected to earth ground on the fetal monitor connection end of the cable 330.

Reference 'B' illustrates the logic state table 402 of prior LVDS receivers that are absent the ability to latch off the signal upon first detection of a cable fault. Additionally, prior LVDS receivers are limited to detecting only (1) both the inputs are open, (2) both the inputs are shorted together and (3) both the inputs are un-driven while a termination resistor is intact at the receiver input/the LVDS transmitter (at fetal monitor 302) output is in high impedance state (electrically floating).

The present invention overcomes shortcomings of prior LVDS receivers by providing a fail-safe differential receiver 100 circuits as illustrated in at least FIGS. 3-6.

In an exemplary embodiment and in contrast to prior transducers, in the present invention, the improved fail-safe LVDS differential receiver 100 can be embodied in one or more semiconductor chips 406. In this regard, the fail-safe circuit can be configured and/or otherwise encoded to operate in accordance with the state table in reference 'C'.

In operation, the fail-safe differential receiver 100 outputs a fault condition state that is translated by the FHR monitor as an equipment malfunction error. Such fault condition state errors can be displayed to alert the operator. In the alternative, the improved fail-safe LVDS differential receiver 100 circuits can output the receiver output 143 responsive to a normal operating state condition is detected (cable conductors are physically and electrically intact between the fetal monitor and the LVDS receives both IN+ 127 input and IN− 129 input). The fail-safe differential receiver 100 output can be latchable such that when an error condition is first detected the fail-safe differential receiver 100 output is latched to the fault condition state blocking the receiver output 143 until the system is reset. This prevents temporary error conditions from allowing the operator to believe the FHR monitor 302, cable 330, and transducer 336 are operating correctly.

In an exemplary embodiment, the fail-safe differential receiver 100 functions in accordance with state table 404 including the fault condition state table 402. In operation, one or more semiconductors 406 can be used, as may be required and/or desired in a particular embodiment. Additionally, programmable LVDS and/or latch-capable combinational logic devices 179 can be encoded 185 by flashing or otherwise downloading programmable logic code software 181 to effectuate the desired operation. Such latch-capable combination logic device 179 can be a programmable logic device (PLD), a complex programmable logic device (CPLD), a floating point gate array (FPGA), or other types or kinds of latch-capable combinational logic devices as may be required and/or desired in a particular embodiment.

With reference to FIG. 2, the present invention fail-safe differential receiver 100 is shown in references 'A' and 'C'. In operation, the fail-safe differential receiver 100 circuit not only detects intermittent or broken wire conditions (from cable 330) but also detects both inputs LVDS+/−(twisted pair conductors) open or short-circuited. LVDS+/−(twisted pair conductors) correspond to IN+ 127 input and IN− 129 input.

The output of the fail-safe differential receiver 100, Vout 180 is then received by signal processor 408 which comprises the microcontroller (MCU) or CPLD by way of, as needed, additional comparing, combinational logic gates, latching (such as by flip-flop), tri-state buffering, other types of buffering, or other signal processing circuitry which is illustrated and referred to as signal processor 408. Signal processor 408 can generate DC voltage output 135 which can be used by other circuits.

In an exemplary embodiment, such semiconductor 406 can be fabricated in a form factor and pin-compatible manner so that the fail-safe differential receiver 100 can be a direct semiconductor part replacement in prior transducers that have prior LVDS shortcomings mentioned above. Alternatively, separate fail-safe differential receiver 100 can be incorporated into the existing frontend printed circuit board (PCB) or backend PCB within the transducer to detect cable fault conditions, as may be required and/or desired in a particular embodiment.

In an exemplary embodiment and with reference to reference 'C', state table 404 illustrates a normal operation state table 418 and a fault condition state table 420, an electronic control system 400 can comprise a fail-safe differential receiver 100 having an IN+ input (cable 330 pin 3), an IN− input (cable 330 pin 2), and a Vout output 180. The fail-safe differential receiver 100 provides stable 1 MHz reference clock signal to signal processor 408 of transducer 336 by generating at a control signal 133 during normal operating state until a fault condition state is detected as follows:

when the IN+ 127 input is open (not connected) the control signal 133 is latched to the fault condition state (such as logic high (H));
when the IN− 129 input is open (not connected) the control signal 133 is latched to the fault condition state (such as logic high (H));
when the IN+ 127 input and the IN− 129 input are connected by a first resistance 130 that is configured as an undriven parallel termination, the control signal 133 is latched to the fault condition state (such as logic high (H));
when the IN+ 127 input is shorted to Vcc or ground (GND) the control signal 133 is latched to the fault condition state (such as logic high (H));
when the IN− 129 input is shorted to Vcc or GND the control signal 133 is latched to the fault condition state (such as logic high (H));
when the IN+ 127 input and the IN− 129 input are shorted together the control signal 133 is latched to the fault condition state (such as logic high (H)); and
when only one of the IN+ 127 or the IN− 129 is intermittently open and reconnected the control signal 133 is latched to the fault condition state (such as logic high (H)).

Once latched the signal out 133 logic state remains the same until the fail-safe differential receiver 100 is reset. In this regard, resetting the latch and error condition can be done by way of cycling power on the fetal monitor, replacing the cable 330 which also cycles power on the transducer, or other suitable resetting methods, as may be required and/or desired in a particular embodiment.

For disclosure purposes, the state of the normal operating state and the fault condition state is not particularly limited. In operation, the normal operating logic state can be either high (H) or low (L), and the fault condition state can be the opposite of the normal operating state.

Additionally, the normal operating state is latched on the control signal 133, requiring a reset to clear latching of the control signal 133 when the normal operating state persists on control signal 133 for more than a predetermined error condition time period. In this regard, normal operation 418 sees the difference between IN+ 127 input and IN− 129 input transitioning 416 between greater than or equal to 100 mV and less than or equal to 100 mV causing control signal 133 to transition 416 between the normal operating state and the fault condition state. If the control signal 133 remains at the normal operating state for an extended period of time (exceeding the predetermined error condition time period) something is wrong as illustrated in the state table 420 and the control signal 133 is latched to the normal operating state which stops FHR detection until the transducer 336 is reset. A reset can be done by unplugging the transducer 336 from the fetal monitor 302 (removing power temporarily), changing cables, or other suitable reset methods. The predetermined error condition time period can be set in the range of milliseconds to seconds, as may be required and/or desired in a particular embodiment.

An advantage, in the present invention, is that by latching the control signal 133 when an error condition in the state table 420 is detected, displaying an incorrect FHR is prevented. As one example, the error condition when one of IN+ 127 or IN− 129 is open (not connected) an erroneous waveform can be created that is interpreted by the fetal monitor 302 as an FHR in the range of 60 to 240 beats per minute even when the transducer 336 is not connected to a patient 502. The present invention solves this error condition and others by latching the control signal 133 to the normal operating state when the control signal has been at the normal operating state for a time period that exceeds the predetermined error condition time period preventing incorrect FHR readings from being displayed on the fetal monitor 302 and requiring a technician to remove from service broken cables 330 and/or transducer 336.

Figure 3:
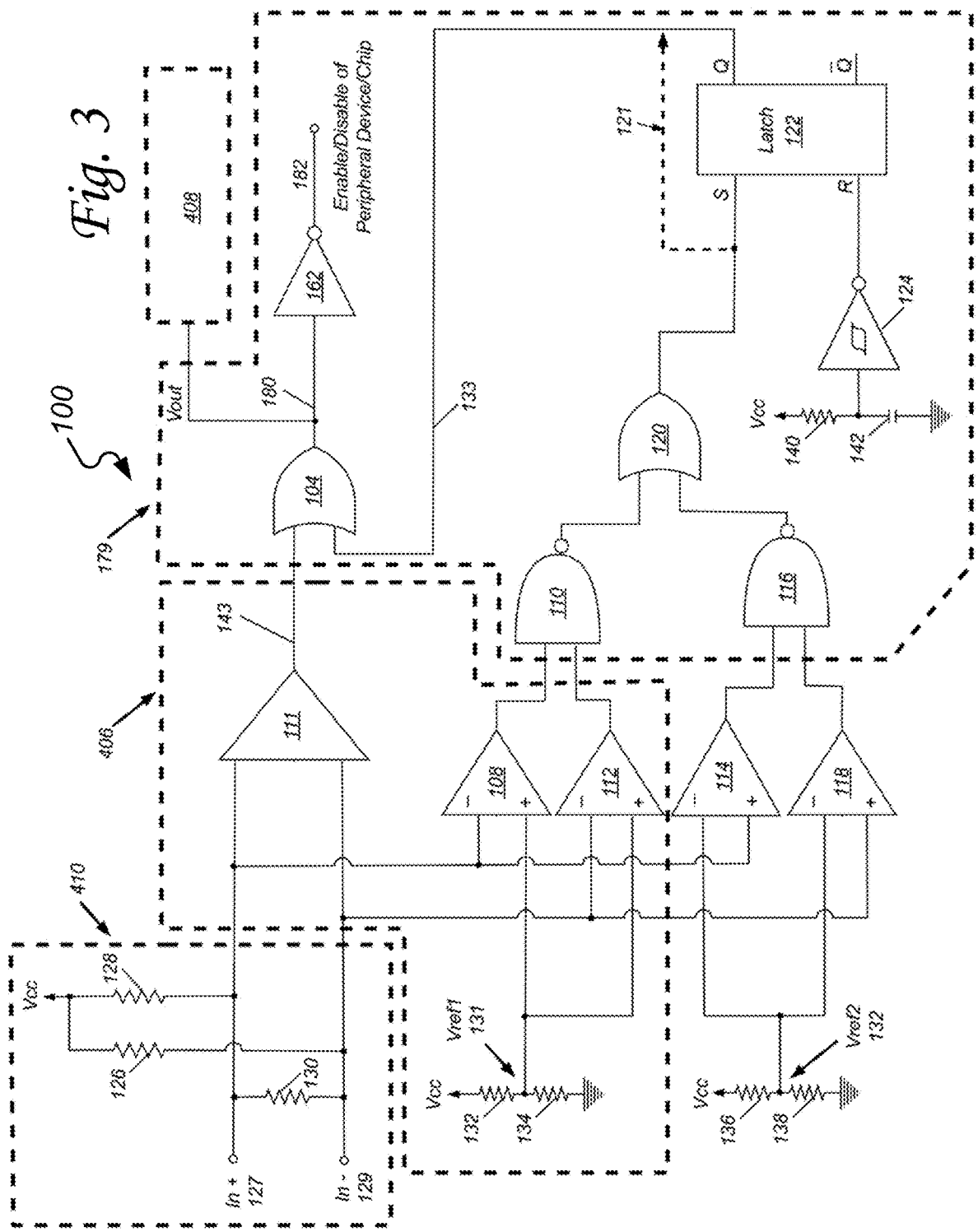
FIG. 3 illustrates one example of a circuit diagram for a fail-safe differential receiver having a latchable control signal interrupt capability.

Referring to FIG. 3, there is illustrated one example of a circuit diagram for a fail-safe differential receiver 100 having a latchable control signal interrupt. In an exemplary embodiment, a transmitter drives a current between IN+ input 127 and IN− input 129, which generates a voltage across the load or terminating resistor 130. This voltage is detected by differential amplifier 111, which receives signals IN+ input 127 and IN− 129 input on its non-inverting and inverting inputs respectively.

In normal operation, control signal 133 input to NOR gate 104 is logic low (normal operating state), so the receiver output 143 from differential amplifier 111 is passed through the OR gate 104 to generate output Vout 180. Output Vout 180 is a digital signal such as a Transistor-Transistor-Level (TTL) signal that may be driven full-rail between power (Vcc) and ground (GND).

The differential signals IN+ 127 and IN− 129 are applied to the inverting inputs of comparators 108 and 112 and the non-inverting inputs of comparators 114 and 118 respectively. The non-inverting inputs of comparators 108 and 112 are driven by a reference voltage Vref1 131, which is configured to be very close to the power-supply voltage Vcc. Resistors 132 and 134 form a voltage divider that generates Vref1 131. The resistance of pull-up resistor 132 is much less than the resistance of pull-down resistor 134, so Vref1 131 is in the range of 97% of Vcc, or 0.97×Vcc in this example. As an example, for a 3.0-volt Vcc, Vref1 131 is 2.91 volts. Of course, resistors 132 and 134 can be adjusted to obtain other values of Vref1 131 near Vcc as may be required and/or desired in a particular embodiment. In general, the best results are obtained when Vref1 131 is as close as possible to Vcc.

In an exemplary embodiment, the first voltage reference 131 comprises a first resistor 132 connected in series with a second resistor 134 creating the first voltage reference 131 at the junction of the first resistor 132 and the second resistor 134. The first resistor 132 connects at one end to Vcc and the second resistor 134 connects at one end to GND. Values of the first resistor 132 and the second resistor 134 are selected such that the first voltage reference 131 is in the range of 97% of Vcc.

The inverting inputs of comparators 114 and 118 are driven by a reference voltage Vref2 132, which is configured to be very close to the ground (GND). Resistors 136 and 138 form a voltage divider that generates Vref2 132. The resistance of pull-down resistor 138 is much less than the resistance of pull-up resistor 136, so Vref2 132 is in the range of 0.03% of Vcc, or 0.03×Vcc in this example. For a 3.0-volt Vcc, Vref2 is 0.09 volts. Of course, resistors 136 and 138 can be adjusted to obtain other values of Vref2 132 near GND as may be required and/or desired in a particular embodiment. In general, the best results are obtained when Vref2 132 is close to GND.

In an exemplary embodiment, the second voltage reference 132 comprises a third resistor 136 connected in series with a fourth resistor 138 creating the second voltage reference 132 at the junction of the third resistor 136 and the fourth resistor 138. The third resistor 136 connects at one end to Vcc and the fourth resistor 138 connects at one end to GND. Values of the third resistor 138 and the fourth resistor 138 are selected such that the second voltage reference 132 is in the range of 0.03% of Vcc.

During normal operation, bias resistors 410 pull-up resistors 126 and 128 have large resistance values in the 500K ohm range and thus produce small electrical currents. The electrical current through the terminating resistor 130 is much greater than the pull-up resistor electrical currents, so their effect is negligible.

During normal operation, IN+ 127 and IN− 129 inputs are each below Vref1 131, since Vref1 131 is close to Vcc, such as previously disclosed in the range of 0.97×Vcc, and IN+ 127 and IN− 129 typically switch near Vcc/2, and comparator 108 and 112 output are a logic level high (H) since Vref1 131 is above IN+ 127 input and IN− 129 input. Both the inputs of NAND gate 110 being a logic high (H), drive its output logic low (L). The output of the NAND gate 110 is one of the inputs of OR gate 120. The other input of OR gate 120 is also logic low (L) due to the fact that Vref2 132 is close to GND potential as previously disclosed in the range of 0.03×Vcc. Vref2 132 is applied to the inverting inputs of comparators 114 and 118, and their non-inverting inputs are higher than Vref2 132 so that both comparators 114 and 118 produce a logic high (H) output making both inputs of NAND gate 116 logic high (H) which gets inverted to a logic low (L) as a second input to OR gate 120. Hence the output of OR gate 120 is logic low (L) during normal operation and acts as SET (S) input to the SR latch 122. Just after power on, a long RC time constant formed by resistor 140 and capacitor 142 is coupled to hex buffer 124 the output of which interconnects with the RESET (R) input of latch 122 raising the RESET (R) line logic high (H) momentarily while SET (S) input is logic low (L) (by the time supply voltage stabilizes). The 'Q' output of latch 122 is driven logic low (L) and latches to the logic low (L) level, as the RESET (R) input permanently transitions to a logic low level as the capacitor 142 charges to Vcc. This low 'Q' output forms the control signal 133 which is an input to the OR gate 104 and acts as a control to allow or block the signal at its other input from the differential amplifier 111 to pass to the output as Vout 180. An inverter 162 receives the output Vout 180 from the OR gate 104 and is inverted forming Enable/Disable control signal 182 output for the peripheral devices/chips.

During operation, the differential amplifier 111 receiver output 143 is allowed to pass through to the output Vout 180 when the control signal 133 is a logic low (L) indicating a normal operating state. In the alternative, when the control signal 133 is a logic high (H) indicating a fault condition state, the control signal 133 is passed holding Vout logic (H) and blocking or otherwise terminating the operation of the FHR transducer 336 until the fault condition is corrected and the fail-safe differential receiver's 100 latch 122 is reset.

Figure 8:
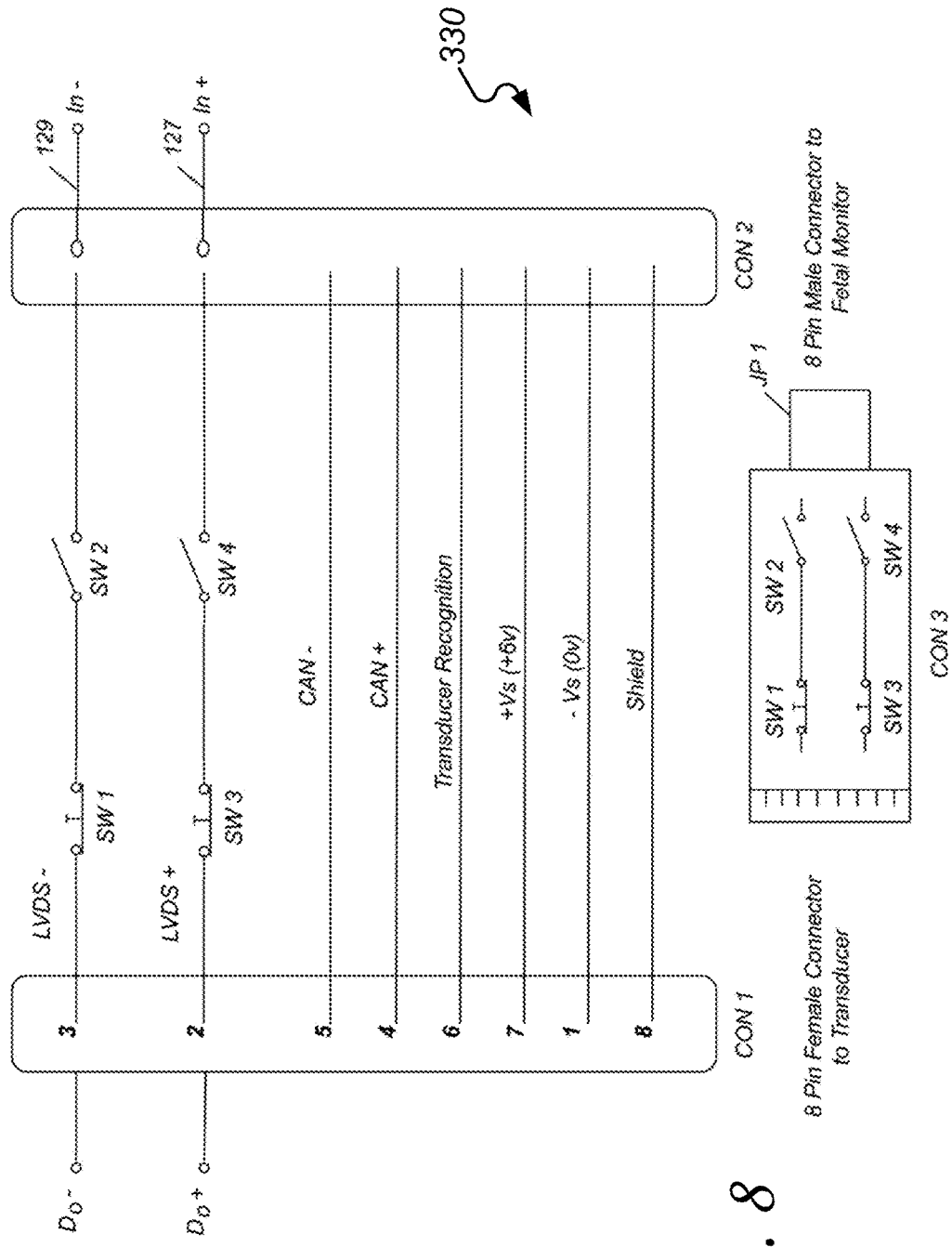
FIG. 8 illustrates one example of a communication cable schematic with LVDS line testing capabilities.

In an exemplary embodiment of an IN+ 127 fault condition detection and with reference to FIGS. 3 and 8, in operation, consider an open cable 330 conductor connecting LVDS+ transmitter output Do+, by way of the cable 330, to the IN+ 127 input of the differential amplifier 111. The IN+ input 127 tries to pull-up to Vcc through resistor 128 making the inverting input voltage higher than Vref1 131 (2.91V) on the non-inverting input of comparator 108 that results in comparators 108 output switching to a logic low (L). This means one input of the NAND gate 110 switches to a logic low (L), forcing its output to switch to logic high (H), and as a result, the OR gate 120 output switches to a logic high (H), which triggers the latch 122 switching the 'Q' output also referred to as the control signal 133 to a logic high (H) and as an input to the OR gate 104, blocks the differential amplifier 111 receiver output 143 from reaching Vout 180 effectively stopping the operation of the FHR transducer 336.

During this faulty condition, the NAND gate 116 output remains logic low (L) as the non-inverting input of both comparators 114 and 118 remain at a higher voltage level than the Vref2 132 (0.09V). If the cable connection to IN+ 127 is restored under this situation, comparator 108 output is restored to logic high (H) as its inverting input is below Vref1 131 (2.91V) on non-inverting input. As such NAND gate 110 outputs switches to a logic low (L) and in turn OR gate 120 output switches to a logic low (L) on SET (S) input of latch 122. Since the RESET (R) input is a logic low (L), the output Q which is the control signal 133 latches to the previous logic high (H) continuing to block the differential amplifier 111 receiver output 143 until power Vcc is switched 'OFF' and 'ON' again.

In an exemplary embodiment of an IN− 129 fault condition detection and with reference to FIGS. 3 and 8, in operation similar logical operational explanation would apply if the other input IN− 129 input is open (unconnected) and IN+ 127 input is intact (connected) and OR gate 104 would block the receiver output 143.

As referenced in FIG. 3, some prior LVDS receivers included a frontend 410 and first-stage receiver 406 but these sections 406/410 are not sufficient for fault detection of a single IN+ 127 or IN− 129 disconnection. In this embodiment and an advantage in the present invention is the circuitry beyond sections 406/410 that effectuates the single differential input (IN+ 127 or IN− 129) disconnect detection with latchable control signal 133 interrupt capability.

A shortcoming of prior LVDS receives that only utilize sections 406/410 is that when either of the inputs (IN+ 127 or IN− 129) is open (unconnected), the remaining connected input has a common mode DC voltage (as an example 2.2V for Philips ultrasound transducer models M2736A, M2736AA, REF #867246) being driven from the LVDS transmitter at the FHR monitor 302 side of the cable 330 connection. This common mode DC voltage appears through the termination resistor 130, which is in the range of 100 ohm to 120 ohm, to the open input end (the disconnected IN+ 127 or IN− 129 end) and hence does not get pulled-up to Vcc. As such, comparators 108 and 112 cannot be switched to output a logic low (L) when one of the LVDS inputs (either IN+ 127 or IN− 129) is open. The present invention overcomes this limitation.

With reference to FIGS. 3 and 8, an exemplary embodiment of both IN+ 127 input and IN− 129 input disconnect fault condition detection follows. If cable 330 is open to both IN+ 127 input and IN− 129 input at the same time, there is no drive from the LVDS transmitter on the FHR monitor 302 side of cable 330, no current flows through the termination resistor 130 or pull-up to Vcc resistors 126 and 128 which are connected to IN− 129 and IN+ 127 respectively. In this fault condition, the inverting inputs of both comparators 108 and 112 switch to a logic high (H) producing a logic low (L) at their outputs which are also the NAND gate 110 inputs. The NAND gate 110 output switches to a logic high (H) which is received at the input of OR gate 120. The logic high (H) on the OR gate 120 input causes the OR gate 120 output to switch to a logic high (H). The OR gate 120 output logic high (H) is received at the latch 122 SET (S) input causing the 'Q' output also referred to as the control signal 133 to switch and remain latched to a logic high (H) state. The control signal 133 logic high (H) state is received at the input to OR gate 104 causing the OR gate 104 output to switch to a logic high (H) effectively blocking the difference signal 143 and inactivating the FHR transducer 336 until the fault condition is corrected and the fail-safe receiver 100 is reset.

In the present invention, an advantage is that even if the open IN+ 127 input and IN− 129 input connections are restored and the voltages of inverting inputs of comparators 108 and 112 return to normal voltage levels such that the SET (S) input of latch 122 is switch to a logic low (L) the latch 122 'Q' output remains latched to the earlier state of logic high (H) state blocking the receiver output 143 and continuing to disable the FHR transducer 336 until the power is reset causing the latch 122 to reset. In this regard, on the first occurrence of a cable fault, the FHR transducer 336 is disabled preventing false FHR readings 326/324 from being communicated to the FHR monitor 302 and displayed as frequently happens with prior LVDS receivers that are absent the advantages in the present invention of control signal 133 latching capabilities.

With reference to FIGS. 3 and 8, an exemplary embodiment of both IN+ 127 input and IN− 129 input shorted fault condition detection follows. If the cable 330 conductor shorts IN+ 127 input and IN− 129 input together, no current flows through resistor 130 or the pull-up resistors 126 and 128 that pull-up IN+ 127 input and IN− 129 input to Vcc respectively. In this fault condition, inverting inputs of both comparators 108 and 112 switches to a logic high (H) producing a logic low (L) at their outputs which are inputs to NAND gate 110 causing the NAND gate 110 output to switch to a logic high (H). The output of the NAND gate 110 which is a logic (H) passes to the input of the OR gate 120 whose other input is a logic low (L), resulting in the output of the OR gate 120 switching to a logic high (H). The OR gate 120 output logic high (H) is received at the latch 122 SET (S) input causing the 'Q' output also referred to as the control signal 133 to switch and remain latched to a logic high (H) state. The control signal 133 logic high (H) state is received at the input to OR gate 104 causing the OR gate 104 output to switch to a logic high (H) effectively blocking the difference signal 143 and inactivating the FHR transducer 336 until the fault condition is corrected and the fail-safe receiver 100 is reset.

In the present invention, an advantage is that even if the shorted IN+ 127 input and IN− 129 input connections are restored and the voltages of inverting inputs of comparators 108 and 112 return to normal voltage levels such that the SET (S) input of latch 122 is switch to a logic low (L) the latch 122 'Q' output remains latched to the earlier state of logic high (H) state blocking the receiver output 143 and continuing to disable the FHR transducer 336 until the power is reset causing the latch 122 to reset. In this regard, on the first occurrence of a cable fault, the FHR transducer 336 is disabled preventing false FHR readings 326/324 from being communicated to the FHR monitor 302 and displayed as frequently happens with prior LVDS receivers that are absent the advantages in the present invention of control signal 133 latching capabilities.

With reference to FIGS. 3 and 8, an exemplary embodiment when one of the IN+ 127 or IN− 129 is shorted to Vcc or greater voltage fault condition detection follows. If one of cable 330 conductors, either IN+ 127 or IN− 129 shorts to a conductor that supplies DC power voltage equal to or greater than Vcc, the inverting input voltage of either comparator 108 or 112 will be higher than Vref1 131 on their respective non-inverting input. Correspondingly, the output of comparators 108 and 112 output will switch to a logic low (L) causing NAND gate 110 output to switch to a logic high (H), which in turn causes the output of OR gate 120 to switch to a logic high (H). The OR gate 120 output logic high (H) is received at the latch 122 SET (S) input causing the 'Q' output also referred to as the control signal 133 to switch and remain latched to a logic high (H) state. The control signal 133 logic high (H) state is received at the input to OR gate 104 causing the OR gate 104 output to switch to a logic high (H) effectively blocking the difference signal 143 and inactivating the FHR transducer 336 until the fault condition is corrected and the fail-safe receiver 100 is reset.

In the present invention, an advantage is that even if the shorted to Vcc IN+ 127 or IN− 129 connection is restored and the voltages of inverting inputs of comparators 108 and 112 return to normal voltage levels such that the SET (S) input of latch 122 is switch to a logic low (L) the latch 122 'Q' output remains latched to the earlier state of logic high (H) state blocking the receiver output 143 and continuing to disable the FHR transducer 336 until the power is reset causing the latch 122 to reset. In this regard, on the first occurrence of a cable fault, the FHR transducer 336 is disabled preventing false FHR readings 326/324 from being communicated to the FHR monitor 302 and displayed as frequently happens with prior LVDS receivers that are absent the advantages in the present invention of control signal 133 latching capabilities.

With reference to FIGS. 3 and 8, an exemplary embodiment of when one of the IN+ 127 or IN− 129 is shorted to the shield of the cable 330 fault condition detection follows. If one of cable 330 conductors, either IN+ 127 or IN− 129 shorts to the cable 330 shield, the non-inverting input voltage of either comparator 114 and 118 will be lower than Vref2 132 which is applied to their respective inverting inputs. As a result, the output of either comparator 114 or 118 will switch to a logic low (L) causing the output of NAND gate 116 to switch to a logic high (H), which in turn causes the output of OR gate 120 to switch to a logic high (H). The OR gate 120 output logic high (H) is received at the latch 122 SET (S) input causing the 'Q' output also referred to as the control signal 133 to switch and remain latched to a logic high (H) state. The control signal 133 logic high (H) state is received at the input to OR gate 104 causing the OR gate 104 output to switch to a logic high (H) effectively blocking the difference signal 143 and inactivating the FHR transducer 336 until the fault condition is corrected and the fail-safe receiver 100 is reset.

In the present invention, an advantage is that even if the shorted to cable 330 shield IN+ 127 or IN− 129 connection is restored and the voltages of inverting inputs of comparators 108 and 112 return to normal voltage levels such that the SET (S) input of latch 122 is switched to a logic low (L) the latch 122 'Q' output remains latched to the earlier state of logic high (H) state blocking the receiver output 143 and continuing to disable the FHR transducer 336 until the power is reset causing the latch 122 to reset. In this regard, on the first occurrence of a cable fault, the FHR transducer 336 is disabled preventing false FHR readings 326/324 from being communicated to the FHR monitor 302 and displayed as frequently happens with prior LVDS receivers that are absent the advantages in the present invention of control signal 133 latching capabilities.

In an exemplary embodiment and with reference to FIG. 3, a jumper connection 121 can be utilized to include or exclude the latch 122 capability. Such a jumper connection 121 can be useful during cable or transducer 330 testing and at other times when avoiding a power cycle reset to reset a latched latch 122 is desired.

In an exemplary embodiment, the fail-safe differential receiver 100 comprises a differential amplifier 111. The differential amplifier 111 comprises a receiver output 143 and receives an IN+ input 127, and an IN− input 129. A first combining gate 104 receives the receiver output 143, a control signal 133, and generates a Vout 180 output.

The fail-safe differential receiver 100 further comprises a first reference voltage 131 and a first comparator 108. The first comparator 108 receives the IN+ input 127 and the first reference voltage 131 and generates a first compare signal. A second comparator 112 receives IN− input 129 and the first reference voltage 131, and generates a second compare signal. A second combining gate 110 receives the first compare signal and the second compare signal and generates a third compare signal.

The fail-safe differential receiver 100 further comprises a second reference voltage 132 and a third comparator 114. The third comparator 114 receives the IN+ input 127 and the second reference voltage 132 and generates a fourth compare signal. A fourth comparator 118 receives the IN− input 129 and the second reference voltage 132 and generates a fifth compare signal. A third combining gate 116 receives the fourth compare signal and the fifth compare signal and generates a sixth compare signal. A fourth combining gate 120 receives the third compare signal and the sixth compare signal and generates a seventh compare signal. And a latch 122 receives the seventh compare signal and generates the control signal 133. The control signal 133 transitions between a normal operating state and a fault condition state.

In operation, the receiver output 143 is applied to a Vout 180 output as long as the control signal 133 is in the normal operating state, and on the first occurrence of the fault condition state the latch 122 latches blocking the receiver output 143 from being applied to Vout 180 output until the latch is reset.

In an exemplary embodiment, a fail-safe differential receiver 100 comprises a first voltage reference 131, a second voltage reference 132, and a differential amplifier 111. The differential amplifier 111 comprises a receiver output 143 and receives an IN+ input 127, and an IN− input 129. The fail-safe differential receiver 100 comprises more than one comparator 108/112/114/118. Each of the comparators 108/112/114/118 comprises a compared output and receives at least two of the following: the IN+ input 127, the IN− input 129, the first voltage reference 131, or the second voltage reference 132. A latch-capable combinational logic device 179 receives each of the compared outputs, and the receiver output 143. The latch-capable combinational logic device 179 comprises a latch 122, and a control signal 133 that is switched to a normal operating state until at least one of the following is detected:

when the IN+ input and the IN− input are connected by a first resistance 130, which is configured as an undriven parallel termination, the control signal 133 is latched to the fault condition state;

when the IN+ input is shorted to Vcc or GND the control signal 133 is latched to the fault condition state;

when the IN− input is shorted to Vcc or GND the control signal 133 is latched to the fault condition state; and when the IN+ input and the IN− input are shorted together the control signal 133 is latched to the fault condition state.

In operation, the receiver output 143 is applied to a Vout 180 output as long as the control signal 133 is in the normal operating state, and on the first occurrence of the fault condition state, the latch 122 latches blocking the receiver output 143 until the latch is reset.

In an exemplary embodiment, the latch-capable combinational logic device 179 comprises one or more of an OR gate, one or more of a NOR gate, one or more of an AND gate, one or more of a NAND gate, or one or more of an inverter.

Figure 4:
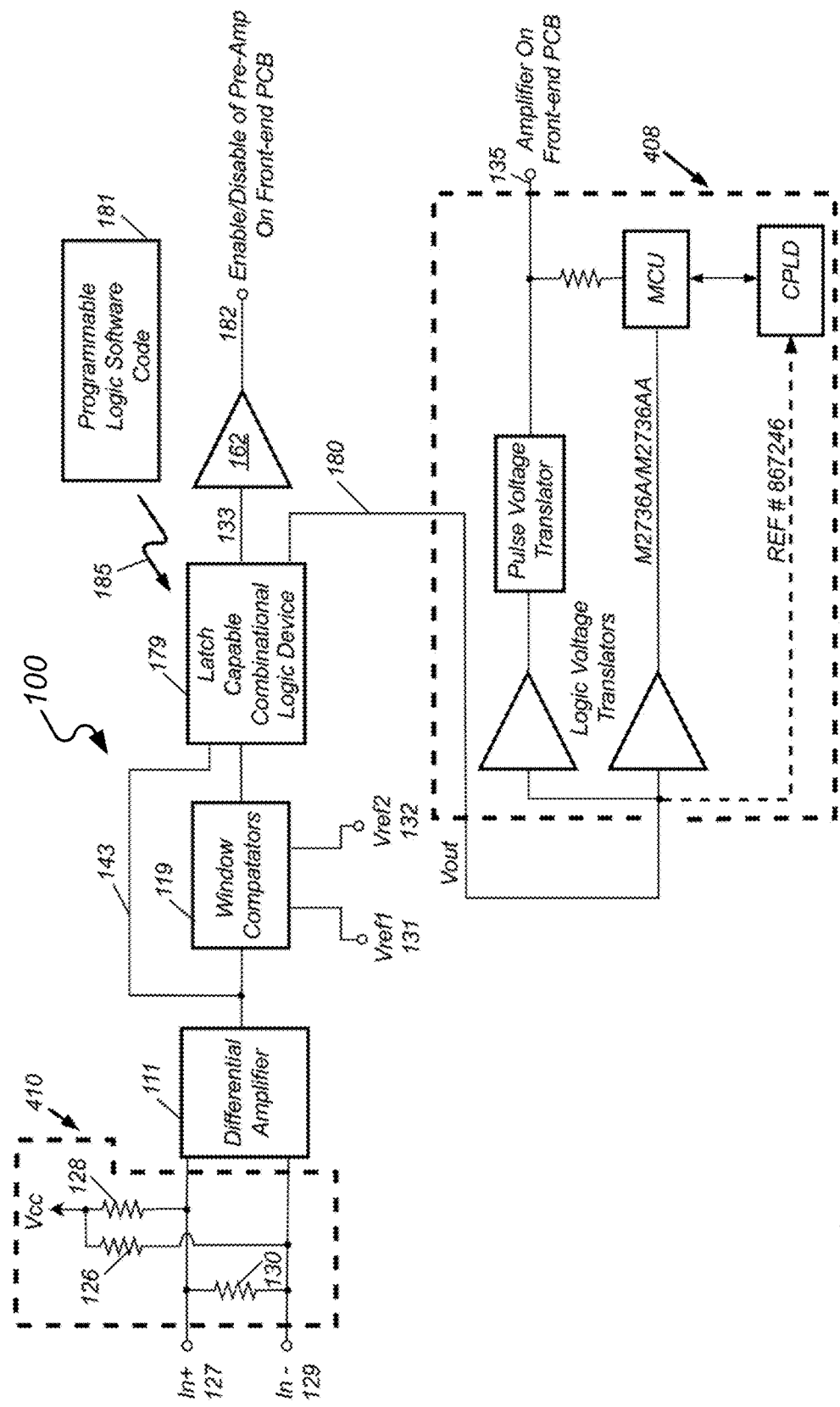
FIGS. 4-5 illustrate examples of a system diagram for a fail-safe differential receiver having single differential input disconnect detection with a latchable control signal interrupt capability.

Referring to FIG. 4, there is illustrated one example of a system diagram for a fail-safe differential receiver 100 having single differential input disconnect detection with a latchable control signal interrupt. In an exemplary embodiment, during normal operation, bias resistors 410 pull-up resistors 128 and 128 have large resistance values in the 500K ohm range or other suitable range and thus produce small electrical currents. The electrical current through the terminating resistor 130 is much greater than the pull-up resistor electrical currents, so their effect is negligible.

Figure 5:
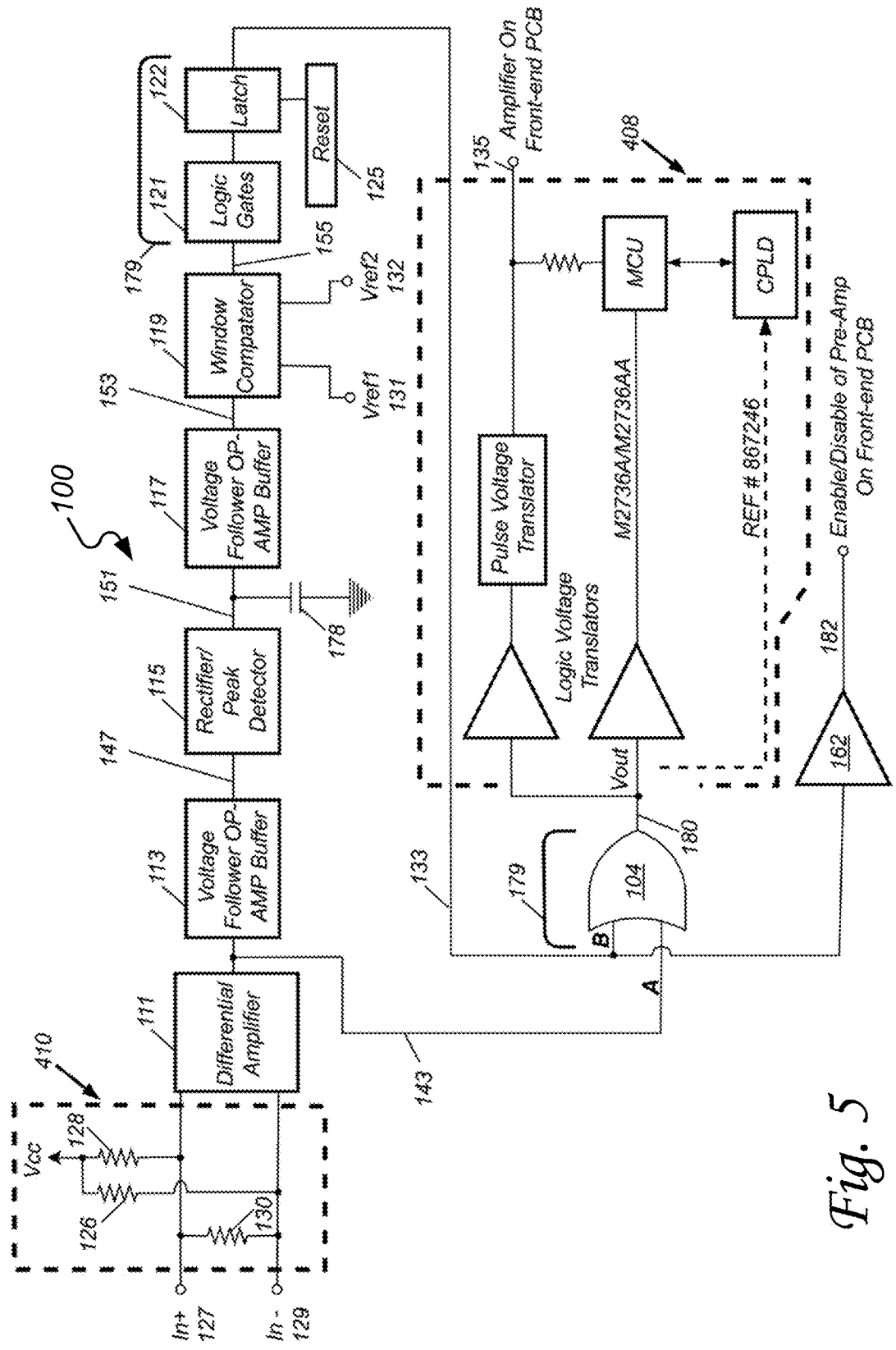
Figure 6:
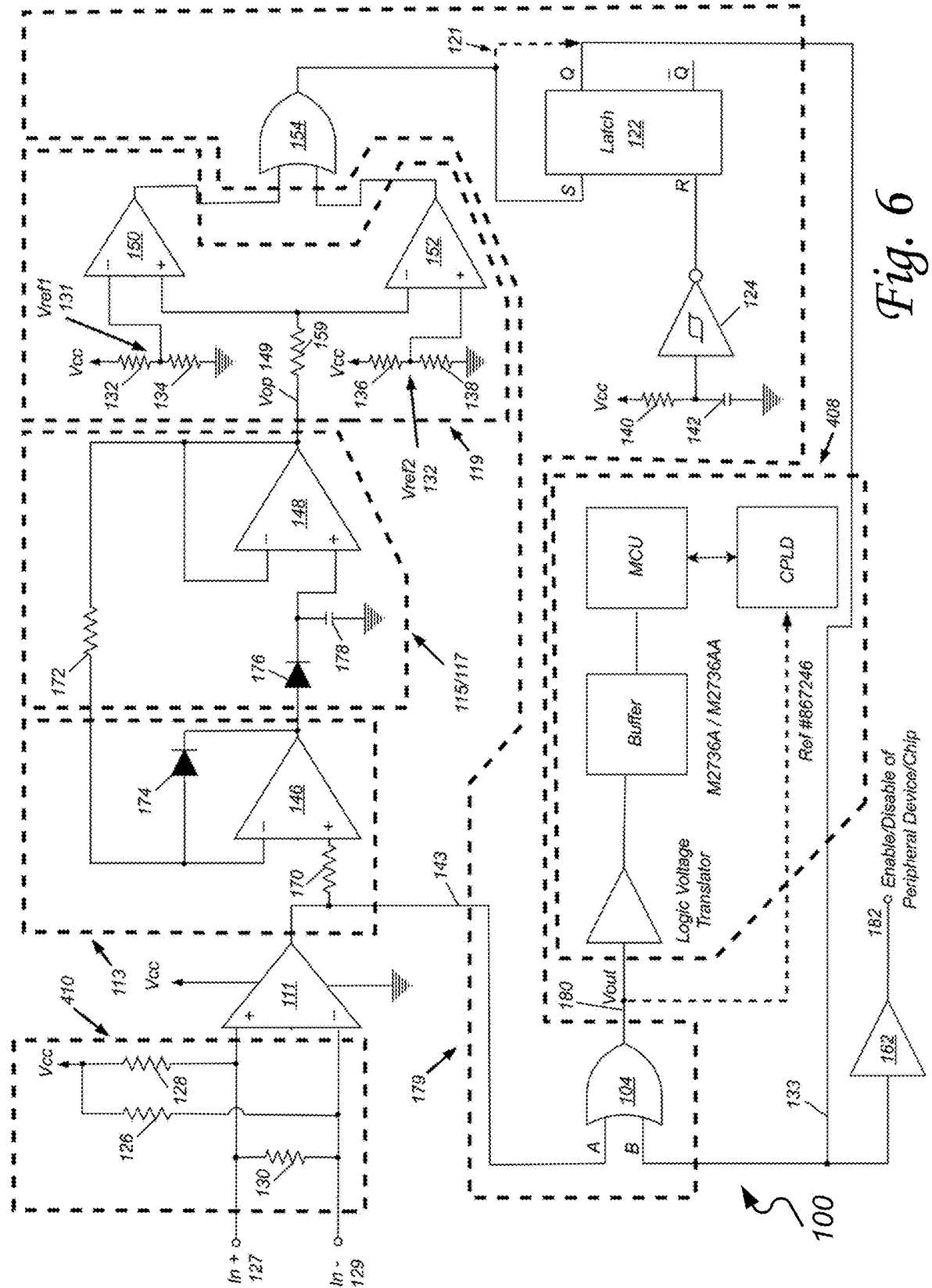
FIG. 6 illustrates one example of a circuit diagram for a fail-safe differential receiver having single differential input disconnect detection with a latchable control signal interrupt capability.

In operation, the differential amplifier 111 receives IN+ 127 input and IN− 129 input and generates a receiver output 143. The op-amp window detector/comparator 119 comprises Vref1 131 and Vref2 132. An op-amp window detector/comparator 119 can be configured with comparators 108/112/114/118 as illustrated in FIG. 3, be configured with voltage follower op-amp buffer 113, rectifier/peak detector 115, and voltage follower op-amp buffer 117 as illustrated in FIGS. 5 and 6, or configured in other suitable ways as may be required and/or desired in a particular embodiment.

Inputs to a latch-capable combinational logic device 179 can include the receiver output 143 and at least one window detector/comparator 119 output. The latch-capable combinational logic device 179 can be one or more programmable logic devices, floating point gate arrays, or other suitable programmable logic devices as may be required and/or desired in a particular embodiment. In an exemplary embodiment, a programmable logic software code 181 can be created. In this regard, programming languages such as VHDL, CUPL, and other suitable programming languages can be used to write logic software. The programmable logic software code 181 can then be encoded 185 or otherwise programmed into the latch-capable combinational logic device 179 causing the latch-capable combinational logic device 179 to operate in accordance with the state table 404 including the fault conditions 420, and in accordance with other aspects of the present invention.

Additionally, the control signal 133 can be inverted by inverter 162 to create an enable/disable peripheral device/semiconductor 182 that can be used to control other semiconductors and/or peripheral devices as may be required and/or desired in a particular embodiment.

The output of the LVDS, Vout 180 is then received by the microcontroller (MCU) or CPLD by way of, as needed, additional comparing, combinational logic gates, latching (such as by flip-flop), tri-state buffering, other types of buffering, or other signal processing circuitry which is illustrated and referred to as signal processor 408. Signal processor 408 can generate DC voltage output 135 which can be used by other circuits.

Referring to FIG. 5 there is illustrated one example of a system diagram and FIG. 6 a circuit diagram for a fail-safe differential receiver having single differential input disconnect detection with a latchable control signal interrupt capability.

A shortcoming of prior LVDS receivers is fault detection for a single input open (disconnected), either IN+ input or IN− input, while the other input is being driven from the LVDS transmitter on the fetal monitor 302 end of cable 330. In this regard, prior LVDS detection circuits tested found that it was not possible to detect the fault condition when only one input IN+ 127 or IN− 129 input is open (disconnected) and the termination resistor at the LVDS input is intact. Stated differently, as long as one end of the termination resistor is driven by the LVDS transmitter, the common mode DC voltage from the LVDS driver appears on the unconnected IN+ input or IN− input end of the termination resistor thereby preventing both ends from being pulled, by pull-up resistors 126/128, to Vcc making single differential input open circuit fault detection not possible.

As such, prior LVDS line receivers and circuits don't support fault detection for single input open (disconnected) conditions. No matter the methods of fault detection at the input of prior LVDS receivers, whether using external resistor biasing or comparators or differential receivers, or a combination of external biasing with an active parallel circuit; the single input (IN+ input or IN− input) open (disconnected) fault detection is not possible with prior LVDS devices, circuits, and methods. As a result, industry standards for prior LVDS receivers support only three fault detection conditions (1) both the IN+ 127 input and IN− 129 input open, (2) both the IN+ 127 input and IN− 129 input shorted together, and (3) both the IN+ 127 and IN− 129 inputs are undriven with a termination resistor at the input.

A shortcoming of prior LVDS receivers and an advantage in the present invention is to be able to detect the fault condition of a single differential input (IN+ 127 or IN− 129) disconnect in combination with a latchable control signal 133 interrupt to disable the FHR transducer 336 on a first occurrence of a fault condition. Absent this feature and a shortcoming of prior LDVS receivers, intermittent behavior, and spurious noise can cause faulty FHR readings 326/324 such as incorrect even excessively high FHR readings 326/324. In this regard, FHR transducers that rely on prior LVDS receivers such as Philips Avalon fetal heart rate ultrasound transducer models M2736A, M2736AA, REF #867246 can give spurious/intermittent wrong fetal heart rate (FHR) reading when a cable goes through intermittent break-make of conductors yielding a temporary or permanent open circuit condition of a single input IN+ input or IN− input at the prior LVDS line receiver on the back-end circuit board (Main CPU PCB) signal processor 408 inside the transducer head.

The present invention overcomes this shortcoming of prior LVDS receivers with the circuit diagrams for a fail-safe differential receiver 100 having single differential input disconnect detection with a latchable control signal interrupt illustrated in at least FIGS. 5 and 6. In an exemplary embodiment, all of the fail-safe fault detection conditions are satisfied in the state table 404 and specifically fault condition state table 420 which is better illustrated in FIG. 2.

With reference to the fault condition state table 420, one of the most critical fault conditions to detect is the single input IN+ 127 or IN− 129 open (disconnected) at the differential amplifier 111 while the termination resistor 130 is in the circuit. In the present invention, an advantage is the use of a second OR gate 104 where input 'A' interconnects with the differential amplifier 111 receiver output 143, and input 'B' interconnects with the latch 122 'Q' output that is also referred to as the control signal 133. During operation, the OR gate 104 output Vout 180 follows the difference signal 143 on input 'A' when the control signal 133 on input 'B' is a logic level (L) (normal operating state), and the OR gate 104 output 180 follows the control signal 133 when a logic high (H) (fault condition state) when a fault condition is detected causing the latch 122 'Q' output/control signal 133 to latch and stay logic high (H) effectively blocking operation of he FHR transducer 336 until the latch 122 is reset such as by a power 'OFF'/'ON' cycle or other suitable methods. A logic voltage translator can be used to receive OR gate 104 output Vout 180 to create a transducer control signal that is used to interface with the electronics within the FHR transducer 336. Additionally, the control signal 133 can be inverted by inverter 162 to create an enable/disable peripheral device/semiconductor 182 that can be used to control other semiconductors and/or peripheral devices, as may be required and/or desired in a particular embodiment.

With reference to FIGS. 5 and 6, a frontend 410 conditions IN+ input 127 and IN− input 129 to differential amplifier 111. The front end 410 comprises pull-up resistors 126/128 and termination resistor 130. The receiver output 143 from the differential amplifier 111 is coupled to a voltage follower 113. The voltage follower 113 comprises an op-amp buffer 146, resistor 170, and diode 174. The voltage follower 113 is coupled 147 to a rectifier/peak detector 115 (comprises diode 176 and capacitor 178) and the rectifier/peak detector 115 is coupled 151 to a voltage follower op-amp buffer 117. The rectifier/peak detector 115 and the voltage follower op-amp buffer 117 comprise an op-amp buffer 148, a diode 176, a capacitor 178, a feedback resistor 172 between the output of the second op-amp buffer 148 and the inverting input of the first op-Amp buffer 146, the feedback resistor 172 provides better circuit stability. The voltage follower op-amp buffer 117 is coupled 153 to an op-amp window detector/comparator 119. The op-amp window detector/comparator 119 comprises resistor 159, Vref1 131 formed with resistors 132/134, Vref2 132 formed with resistors 136/138, and op-amp comparators 150/152. The op-amp window detector/comparator 119 is coupled 155 to the logic gates/latch 179. The logic gates/latch 179 comprises logic gates 121 which is coupled to the latch 122. A latch reset 125 is coupled to the latch 122. The 'Q' output of the latch 122 is also referred to as the control signal 133. The logic gates/latch 179 also comprises OR gate 104. The control signal 133 and receiver output 143 are inputs to OR gate 104. During operation, the OR gate 104 output 180 follows the difference signal 143 on input 'A' when the control signal 133 on input 'B' is a logic level (L) (normal operating state), and the OR gate 104 output 180 follows the control signal 133 when a logic high (H) (fault condition state) when a fault condition is detected causing the latch 122 'Q' output/control signal 133 to latch and stay logic high (H) effectively blocking operation of the FHR transducer 336 until the latch 122 is reset such as by a power 'OFF'/'ON' cycle or other suitable methods after the corrective action is taken to address the fault such as cable replacement. Logic voltage translators can be used to invert OR gate 104 output 180 to create a transducer control signal that is used to interface with the electronics within the FHR transducer 336. Additionally, the control signal 133 can be inverted by inverter 162 to create an enable/disable peripheral device/semiconductor 182 that can be used to control other semiconductors and/or peripheral devices as may be required and/or desired in a particular embodiment.

Figure 7:
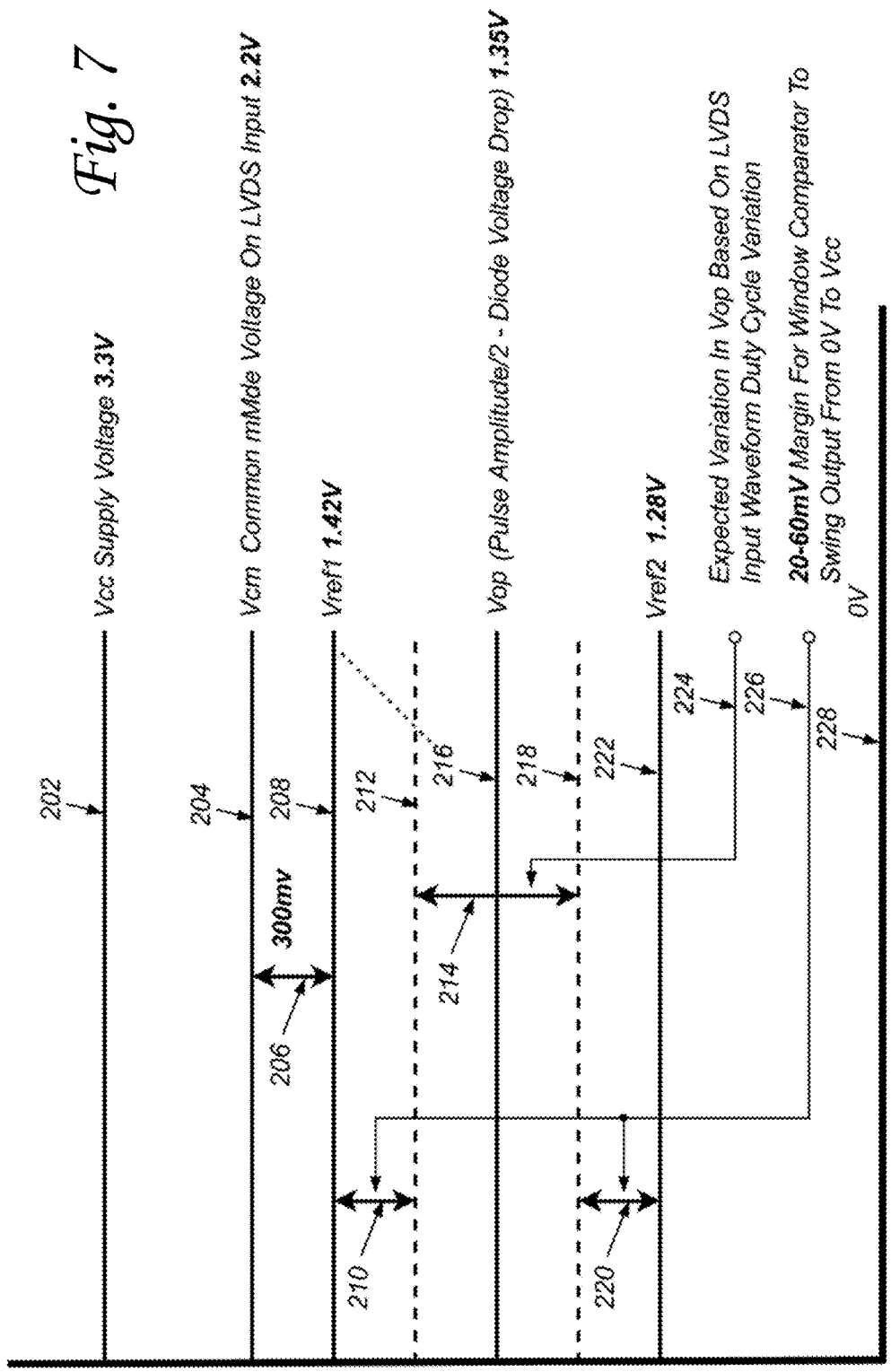
FIG. 7 illustrates one example of a voltage levels diagram for a fail-safe differential receiver having single differential input disconnect detection with a latchable control signal interrupt capability.

In an exemplary embodiment, in the window comparator 119 design, the resistors 132/134/136/138 can be selected such that the reference voltage Vref1 131 and Vref2 132 are in the range of Vop plus the expected variation in millivolt during normal operation in the range of 20 to 60 millivolts margin and Vop minus the expected variation in millivolt during normal operation in the range of 20 to 60 millivolts margin respectively or other suitable value as illustrated in at least FIG. 7. Here Vop is the voltage value during the normal operation as Vcc/2 minus the forward voltage drop across rectifier diode 178. The slight variation of Vop in millivolts during the normal operation is based on the duty cycle change of the normal signal at differential receiver output 143.

In an exemplary embodiment, with regards to the rectifier/peak detector 115, the value of the capacitor 178 should be chosen so that the time constant Rd2×C (Rd2 forward resistance of diode 176×the capacitance of capacitor 178) is higher than the period of the expected input waveform. This value should be 5T or slightly greater (where T is the time period of the output square waveform (the conditioned difference signal 143) from the differential amplifier 111) in order to act as a peak sample hold element of the circuit.

During normal operation, the receiver output 143 is a square waveform with amplitude close to the DC power supply Vcc. The receiver output 143 is coupled to the voltage follower op-amp buffer 113 which is set for unity gain and by way of the voltage follower op-amp buffer 113 coupled to the rectifier/peak detector 115. The rectifier/peak detector 115 outputs a DC voltage level lower than Vcc/2 (input square wave amplitude voltage/2) depending on the voltage drop across the rectifying diode 176 as well as the duty cycle of the input square wave (the conditioned difference signal 143). The output of the rectifier/peak detector 115 is coupled to the input of the window comparator 119 by way of the voltage follower op-amp buffer 117 without any change because the voltage follower op-amp buffer 117 is also a unity gain voltage follower.

The DC voltage level of the square wave (the conditioned difference signal 143) will have a very minute deviation (a few millivolts to tens of millivolts) centered around the DC value obtained when the square wave input (the conditioned difference signal 143) to the rectifier/peak detector stage 115 is in the range of a 50% duty cycle as long as the differential amplifier 111 inputs IN+ 137 and IN− 139 do not have any faults and there is no failure internally to the differential amplifier 111 semiconductor(s). When the differential amplifier 111 is used to distribute a reference clock signal (as in the case of Philips ultrasound transducer models M2736A, M2736AA, ref #867246), the output DC voltage level of the rectifier/peak detector stage 115 is expected to be rock steady indicating a normal function of differential amplifier 111.

The output of the rectifier/peak detector stage 115 is Vop 149 and has a DC voltage level when the input is a square wave (the conditioned difference signal 143) of 50% duty cycle with an amplitude of Vcc. The Vop 149 will be lower than Vcc/2 based on the voltage drop across the rectifying diode 176. The window comparator 119 has two distinct settings of the reference voltage levels. In this regard, during normal operation, Vref1 131 is slightly higher than Vop 149 and Vref2 132 is slightly lower than Vop 149 voltage value. The difference or deviation of these reference voltages Vref1 131 and Vref2 132 from the Vop 149 voltage value should be in the range of 20 to 60 mV more than the expected variation in Vop 149 due to the expected variation in the duty cycle of the square waveform (the conditioned difference signal 143) at the input of the rectifier/peak detector 115 during normal operation of the differential amplifier 111.

The Vref1 131 voltage value (calculated as Vop 149 value plus the expected millivolt variation in Vop 149 during normal operation plus 20-60 millivolt margin). As such Vref 131 should fall at least 300 millivolts below the common mode voltage Vcm drive on the IN+ 127 and IN− 129 inputs of the differential amplifier 111.

For example, and not a limitation, if Vcc=3.3V, 1 MHz 50% duty cycle with 3.3V amplitude reference clock (square waveform which is the conditioned difference signal 143) output of differential amplifier 111. In normal operation, a 2.2V common mode voltage (Vcm) drive on the IN+ 127 and IN− 129 inputs of differential amplifier 111.

In this example, it is expected there will be hardly a +/−10 mV variation in Vop output 149 of the rectifier/peak detector 115 as the reference clock square wave (the conditioned difference signal 143) is configured to be steady during normal operation and considering diode 176 drop to be 0.3V, the Vop output 149 will be in the range of 1.35V (square waveform amplitude 3.3V/2−0.3V diode drop). So, Vref1 131 should be 1.42V (Vop 1.35V+10 mV of expected variation+60 mV maximum margin). This Vref1 131 value of 1.42V is well below the limiting value of 1.9V (Common mode input drive voltage of 2.2V−300 mV=1.9V). Vref2 in this example should be 1.28 V (Vop 1.35V−10 mV expected variation−60 mV maximum margin). In this example, if the common mode voltage drive to LVDS IN+ 127 and IN− 129 inputs would have been 1.65V (Vcc/2) then Vref1 131 voltage of 1.42V is higher than the lower limit of the differential amplifier 111 IN+ 127 and IN− 129 input line swing (common mode voltage 1.65V−300 mV=1.35V which is also the same as Vop 149 value during normal operation). It is important that Vcm be sufficiently higher than Vcc/2 so that there is at least 300 mV difference between Vref1 131 and Vcm in order for window comparator 119 to switch output states when one of the IN+ 127 or IN− 129 inputs of differential amplifier 111 is open resulting in the Vcm value at that moment being presented at the receiver output 143 of the differential amplifier 111. If the application requires Vcm to be Vcc/2, then the voltage follower op-amp buffer 113 (with a very high slew rate) should be chosen so that the 3.3V square pulse amplitude of the receiver output 143 at the input to the voltage follower op-amp buffer 113 is reduced at its output, which is coupled to the input of the rectifier/peak detector 115, to a lower value half-way between Vcc/2 and Vcc, in the range of about 2.5V.

In this example, the Vop 149 will be reduced to 0.95V (square pulse amplitude input to the rectifier/2–the diode drop of 0.3V), and DC voltage inputs below 2.5V will be passed onto the widow comparator 119 without any change. This voltage follower op-amp buffer 113 is followed by rectifier/peak detector 115, and voltage follower op-amp 119 acts as a precision rectifier/peak detector, converting square wave (the conditioned difference signal 143) to a DC voltage level Vop 149 equal to the input waveform amplitude/2 minus the diode 176 voltage drop that is fed to a pair of op-amp comparators 150/152.

Comparator 150 has voltage reference Vref1 131 value set between Vop 149 and common mode drive DC voltage Vcm on the IN+ 127 and IN− 129 inputs of differential amplifier 111. Comparator 152 has reference voltage Vref2 132 set to a value between Vop 149 and GND (0V). Whenever there is a failure/fault condition 420 at the input IN+ 127 or IN− 129 of the differential amplifier 111, the square wave (the difference signal 143) at its output disappears, and either more positive voltage (from Vcm to Vcc) or very low voltage close to ground potential (0V) appears depending on the fault condition. For instance, if one of the IN+ 127 or IN− 129 inputs to the differential amplifier 111 is open (disconnected), its receiver output 143 is a DC level close to Vcm.

Due to an open input IN+ 127 or IN− 129, there may be noise riding on that DC voltage level but the rectifier/peak detector 115 stage chops off the negative half, and the window comparator 119 stage receives more voltage input than the Vcm value (due to the positive peaks of the overriding noise) making comparator 150 with Vref1 131 to switch its output to Vcc. If positive, input IN+ of differential amplifier 111 is shorted to GND/shield, the differential amplifier 111 receiver output 143 switches close to GND voltage, and in turn, the output of comparator 152 with Vref2 132 switches to Vcc.

Both the comparator 150/152 outputs are at low (L) (GND potential) when Vop 149 voltage is between Vref1 131 and Vref2 132 and switches to Vcc when Vop crosses either of the voltage references 131/132 values due to a fault condition 420 at the differential amplifier 111 IN+ 127 or IN− 129 inputs, or failure internally to the differential amplifier 111. In the present invention and an advantage that is not present in prior LVDS receivers is that the fail-safe differential receiver 100 can detect failures that are internal to the differential amplifier.

The outputs of the window comparator 119 are coupled to the logic gates/latch 179. The logic gates/latch 179 comprise logic gates 121 including OR gates 104/154 and latch 122. In operation, comparator 150/152 outputs are coupled to the inputs of OR gate 154, and the output of OR gate 154 is coupled to the SET (S) input of latch 122. The output of OR gate 154 is a logic low (L) state during normal operation of the differential amplifier 111 and switches to a logic high (H) state when one of the fault conditions in table 420 occurs at the differential amplifier 111 IN+ 127 and/or IN− 129 inputs. This logic high (H) input to SET (S) causes the 'Q' output of the latch 122 also called the control signal 133 to latch to a logic high (H) state. As an input to the second OR gate 104, when the signal output 133 switches to a logic high (H) the output of the OR gate 104 follows and also switches into a logic high (H) state indicating a fault condition 420 has been detected and effectively blocking the receiver output 143 from passing, stopping the operation of the FHR transducer as a safety measure and to prevent incorrect FHR readings until the fault condition is removed and the FHR transducer reset such as by cycling power.

During initial power-on or cycling of power 'OFF' and 'ON', a reset circuit which comprises resistor 140, capacitor 142, and inverter 124 holds the RESET (R) pin of the latch 122 high until Vcc becomes stable and then drifts permanently logic low (L) in accordance with the RC 140/142 time constant value selected. The SET (S) pin of the latch 122 is also normally at a logic low state after power is switched 'ON' as the differential amplifier 111 output steadies with a square waveform (the difference signal 143) resulting in Vop 149 voltage input to window comparator 119 settling within the limits of Vref1 131 and Vref2 132, thereby setting the comparators 150/152 outputs logic low (L).

The comparators 150/152 outputs are inputs to the OR gate 154 and a logic low (L) input causes the output to switch to a logic (L). The moment a fault condition 420 occurs internally to differential amplifier 111 or at its IN+ 127 and/or IN− 129 inputs such that either of the IN+ 127 or IN− 127 inputs are open, both the inputs open, one of the inputs is open and the other input shorted to shield/ground or Vcc, both the inputs shorted together, both the inputs shorted together and shorted to ground or Vcc, inputs are un-driven (LVDS driver is in a high impedance state on the FHR monitor side of the cable 330), or the terminating resistor 130 is open (disconnected) a fault condition 420 is detected.

Once one of the fault conditions 420 is detected, the differential amplifier 111 output level switches to a DC voltage level from Vcm to Vcc or close to GND (0V). The DC voltage level is passed through the voltage follower op-amp buffer 113, rectifier/peak detector 115, and the voltage follower op-amp buffer 117 as Vop 149 to the window comparator 119. The window comparator 119 outputs a logic high (H) state to one of the inputs of the OR gate 154 which in turn sets latch 122 'Q' output also called the control signal 133 logic high (H). The control signal 133 is coupled to input 'B' of OR gate 104 and the output of the OR gate 104 switches to a logic high (H) state thereby blocking the receiver output 143 from passage through the OR gate 104 to further FHR transducer 336 signal processor 408.

When any fault/failure condition 420 occurs, and either one or both the inputs of the differential amplifier 111 are open or shorted together or short to either Vcc or shield/earth for a moment, (temporary/sporadic/intermittent) such as the cable 330 conductor breaks (disconnects) and resumes continuity again (such as during cable flexing), the receiver output 143 square waveform at the differential amplifier 111 output changes to a DC voltage level either more than Vcm or close to GND (0V). The DC voltage translates to Vop 149 voltage level crossing either Vref1 131 or Vref2 132. This causes the output of either of the comparators 150/152 to switch to a logic high (H). The logic high (H) is coupled to the input of the OR gate 154 causing the OR gate 154 output to switch to a logic high (H) which is coupled to the SET (S) input of the latch 122 causing the 'Q' output also referred to as the control signal 133 to latch high (H).

In this regard, the fail-safe detection is latched high on the first occurrence of the fault condition 420 thereby blocking the receiver output 143 from passage through the OR gate 104 to further FHR transducer 336 processing circuits. This is an important feature in the present invention and an advantage over prior LVDS receives as such intermittent failures can degrade the signal transmission resulting in false FHR readings. Such false FHR readings can lead to fatal errors in the final throughput of the FHR monitoring and display system 302/324/326 and other critical applications beyond FHR monitoring applications such as medical, analytical, process control, material testing, production line feedback control systems, digital devices such as computers, tablets or other industrial applications. This approach, in the present invention, allows corrective action to be taken (such as replacing cable 330 or transducer 336) at the first occurrence of the intermittent fault condition 420. In addition, this feature allows suspect cables 330 to be quickly checked by flexing along its length and observing whether it triggers fail-safe fault condition 420, blocking the difference signal 143 and/or any random noise from being processed producing adverse and inaccurate results such as spurious fetal heart rate with Philips Avalon Ultrasound transducer models M2736A, M2736AA and ref #867246, and other FHR transducers 336.

The outputs of latch 122, either Q or Q can be used directly or buffered 162 to create an enable/disable control signal 182. The enable/disable control signal 182 can be used by peripheral devices and semiconductors operationally related to the circuit of at least FIG. 6 for an added level of fail-safe feature to avoid unwanted results from certain circuit blocks in the signal processing chain.

In a plurality of exemplary embodiments, depending upon the application/system requirements, the latch 122 with the reset logic circuit 124/140/142 could be eliminated 121 and the output of OR gate 154 can be fed directly to the input of OR gate 104. In operation, the latching feature would be disabled while the fail-safe fault condition 420 detection logic continued to operate. This configuration can be useful when for testing, manufacturing, servicing, and in other cases where cycling power to reset the operation of FHR monitor 302 and/or transducer 336, or other pieces of equipment is desired.

In an exemplary embodiment, the fail-safe differential receiver 100 comprises a first voltage reference 131, a second voltage reference 132, and a differential amplifier 111. The differential amplifier 111 comprises a receiver output 143 and receives an IN+ input 127, and an IN− input 129. A first voltage follower operational amplifier 113 comprises a first op-amp output 147 and receives the receiver output 143. A rectifier peak detector 115 comprises a peak output 151 and receives the first op-amp output 147. A second voltage follower operational amplifier 117 comprises a second op-amp output 153 and receives the peak output 151. A window comparator 119 comprises a window compared output 155 and receives the second op-amp output 153, a first reference voltage 131, and a second reference voltage 132. A latch-capable combinational logic device 179 receives the window compared output and the receiver output 143. The latch-capable combinational logic device 179 comprises one or more logic gates 121, a latch 122, a latch reset 125, and a control signal 133 that is switched to a normal operating state until at least one of the following is detected:
  when the IN+ 127 input is open (not connected) the control signal 133 is latched to the fault condition state;
  when the IN− 129 input is open (not connected) the control signal 133 is latched to the fault condition state;
  when the IN+ 127 input and IN− 129 input are connected by a first resistance 130, which is configured as an undriven parallel termination, the control signal 133 is latched to the fault condition state;
  when the IN+ 127 input is shorted to Vcc or GND the control signal 133 is latched to the fault condition state;
  when the IN− 129 input is shorted to Vcc or GND the control signal 133 is latched to the fault condition state;
  when the IN+ 127 input and the IN− 129 input are shorted together the control signal 133 is latched to the fault condition state; and when only one of the IN+ 127 input or the IN− 129 input is intermittently open and reconnected the control signal is latched to the fault condition state.

In operation, the receiver output 143 is applied to a Vout 180 output as long as the control signal 133 is in the normal operating state, and on the first occurrence of the fault condition state, the latch 122 latches blocking the receiver output 143 until the latch is reset.

Referring to FIG. 7, there is illustrated one example of a voltage levels diagram for a fail-safe differential receiver having single differential input disconnect detection with a latchable control signal interrupt. In an exemplary embodiment, Vcc 202 can be in the range of 3.3V. The Vcm 204 Common mode voltage on the LVDS input IN+ 127 and IN− 129 is in the range of 2.2V. Vref1 131/208 is in the range of 1.42V. The difference 206 between the Vcm and Vref1 131 is in the range of 300 mV. A Vop 216 (Pulse amplitude/2−Diode forward voltage drop) variation to 212/218 is in the range 214 of 1.35V. Vref2 132/222 is in the range of 1.28V. The expected variation 224 of Vop is based on LVDS input waveform duty cycle 214 from 1.35V+/−10 millivolts (1.34V to 1.36V). There is a 20-60 mV margin 226 of reference voltages Vref1/Vref2 to the window comparator to swing the output from 0V to Vcc.

Referring to FIG. 8, there is illustrated one example of a communication cable schematic with LVDS line testing capabilities. One concern in general and more specifically with the Philips Avalon ultrasound transducer models M2736A, M2736AA, Ref #867246 is that while in operation intermittent signals can produce erroneous FHR readings. In this regard, if the cable develops intermittent (and subsequently continuous/permanent) open circuit (connection discontinuity) on either of the conductors carrying 1 MHz reference clock signal IN+ 127 or IN− 129 from fetal monitor FM20/30/40/50 to differential amplifier 111, the FHR transducer generates errant spurious/random fetal heart rate (FHR) readings at the FHR monitor 302 anywhere from 60 to 240 beats per minute.

While one of the IN+ 127 or IN− 129 conductors is disconnected, there is no ultrasound beam transmitted out of the transducer face, which means there is no ultrasound echo Doppler signal received from either the fetus or any tissue/internal organ of the abdomen of the pregnant patient 502. These spurious/intermittent false FHR readings are purely the result of internal circuit noise being processed in absence of the 1 MHz reference clock signal from LVDS receiver output and hence not any limitation of ultrasound Doppler technology or application/end-user/operator error. In other words, transducer 336 continues giving spurious FHR when one of the IN+ 127 or IN− 129 wires is disconnected, no matter what the fetus's condition is. During this time spurious FHR readings are being displayed on fetal monitor 302.

When a Philips Avalon transducer unit of model M2736A/M2736AA/Ref #867246 or other models is suspected to be showing spurious FHR or if a clinical incidence is reported, the testing protocol to confirm the problem and the root cause is as follows:
  Take the transducer unit off the fetal monitor and check the fetal monitor independently following the testing protocol as per the relevant Philips/manufacturer's service manual.
  Try another ultrasound transducer unit (M2736A/M2736AA/Ref #867246) that has the fail-safe LVDS circuit of the present invention incorporated and tested in accordance with Philips specifications as per Food and Drug Administration (FDA) approval documentation.

Ensure that the fetal monitor 302 does not have any problems resulting in spurious/wrong fetal heart readings, as well as any other failures.

And, ensure the 1 MHz reference clock generation circuitry, LVDS driver or some other hardware of the fetal monitor is not the root cause of spurious FHR readings.

The cable 330 from the transducer under test in the above steps, should be connected to another transducer 336 that has a fail-safe LVDS circuit of the present invention incorporated and tested.

Connect the transducer 336 with the cable 330 in question to the fetal monitor 302 and perform a cable 330 flex test 6-8 times to see if the fail-safe circuit triggers and latches, indicating a fault condition. If cable 330 is found to be an issue, check the continuity of each conductor with resistance values and also perform other electrical tests such as insulation, adhering to the original equipment manufacturer (OEM) specifications. Even if cable 330 is found not to have intermittent or permanent conductor open/short problems, test it for all other electrical performance parameters adhering to OEM specifications to ascertain good functionality. Testing cable 330 many times by way of flexing from the strain relief to the fetal monitor 302 end connector is a best practice way to detect cable 330 causes of spurious FHR readings due to intermittent or permanent open circuits of one of its conductors IN+ 127 or IN− 129 that carry the 1 MHz reference clock signal from fetal monitor 302 to the ultrasound transducer 336 circuitry.

In an exemplary embodiment, one way to test the fail-safe detection circuit of the present invention before strapping the transducer to patient 502 for monitoring is to use a connector adapter shown in FIG. 8 CON3. This adapter CON3 has a male connector that is the same as the transducer cable on one end, and the other end has a female socket connector that is the same as the one on the fetal monitor 302 FM20/30/40/50. There are two switches SW2/SW4, and two pushbuttons SW1/SW3. SW1 and SW2 are in series and interconnected with IN1 129, and SW3 and SW4 are in series and interconnected with IN+ 127.

These switches are configured as normally closed contacts. For the test, the adapter is plugged into the fetal monitor 302, the transducer is connected to the adapter, and either SW1 or SW3 momentarily pushbuttons are pressed to simulate either an IN+ input or IN− input disconnect fault. Upon detection of the fault condition transducer 336 should be disabled and there should be no FHR reading on the FHR monitor 302.

To reset the transducer 336, disconnect the transducer 336 from the adapter CON3, wait for 15-20 seconds, and then reconnect the transducer 336 to the adapter CON3 and repeat the test, this time pressing the other switch. Ensure the simulated device error appears on the fetal monitor 302.

Remove the transducer 336 from the adapter CON3, take the adapter CON3 off the FHR monitor 302, and connect the transducer directly to the fetal monitor for use on patient 502. This test procedure ensures that the system of the fetal monitor 302 with the transducer 336 is in good working order and capable of detecting the intermittent or permanent failure of the cable 330 conductors. In operation, and with the fail-safe differential receiver 100 of the present invention, this eliminates spurious FHR readings that occur due to processing random noise when there is no ultrasound beam transmission resultant from a disconnected IN+ 127 or IN− 129 conductor. If the system fails, it would likely be a total failure disabling the transducer output 226 to avoid any clinical FHR misinterpretation.

This fail-safe circuit function test adapter CON3 is also useful to demonstrate to the clinical end user that the transducers models M2736A, M2736AA, Ref #864276 (without the incorporation of prior LVDS circuit) that such transducers are prone to spurious FHR detection the moment there is an intermittent or permanent open circuit in one of the conductors connecting to either IN+ 127 or IN− 129.

The process to do so is to first connect the adapter CON3 to the fetal monitor, then connect the transducer to the adapter, set the FHR sound volume on the fetal monitor to OFF or level '1' (to keep the noise level down) as well as alarm volume to minimum, set either switch SW2 or SW4 to OPEN by sliding away from the fetal monitor (towards transducer end), start the thermal recorder on the fetal monitor and leave the set up undisturbed for an hour or two making sure that the transducer face is up towards the room ceiling and there is no stationary or moving object just above within 4 feet distance. Spurious FHR readings will be seen on the fetal monitor display as well as recorded on thermal paper, alarm will beep occasionally based on set values as if the fetal heart rate is out of range (even though there is no fetus), occasionally monitor may display 'FHR signal loss' but there will not be 'FHR Equip Malf' error that appears with '?' in place of actual FHR value display when both the cable conductors (IN+ input, IN− input) are open. During this test, a hydrophone can be placed on the transducer face to confirm that there is no ultrasound beam transmission out of the transducer head when one of the cable conductors (IN+ input, IN− input) are open intermittently or continuously so that the clinical end user can understand the possibility of various clinical misinterpretation situations due to spurious FHR that includes the possibility of missing detection of dead fetus moment fetus heart stops functioning or shows signs of stress by way of abnormal heart rate. When a clinical incidence is reported that involves a fatality or serious conditions, the first thing that needs to be done is to check the cable from the ultrasound transducer unit that was used prior to the incidence. Such a transducer cable in question can be very quickly tested for intermittent or continuous conductor wire (IN+ input, IN− input) break/physical disconnection/open circuit using another transducer head assembly that has LVDS receiver incorporated with fail-safe detection circuit 100 of this invention and once confirmed, send it with original transducer head to specialized accredited laboratory/agency for further testing. In this regard, in the present invention, an advantage is that the present invention allows quick check and problem confirmation after the incidence reporting or even when the clinical end user is in doubt about the reliability of the clinical throughput of the ultrasound transducer being used.

As a best practice, when evaluating the performance of a transducer 336, a disciplined approach that studies the mechanical, operational, and electrical performance of the transducer 336 should be undertaken. In this regard, below is such a disciplined approach when a transducer 336 is to be evaluated and/or serviced as follows:

Note if any of the PZT discs or other components including cable are non-Philips that would require additional testing to find out whether they comply with OEM specifications (electrical as well as physical/structural) and pertinent medical device compliance regulations or not. The reworked, repaired, rebuilt, refurbished, and remanufactured ultrasound transducer units may also have some modifications done on electrical circuit boards (front-end and back-end main CPU PCB) that have to be documented properly as these modifications may compromise overall circuit performance including wrong/spurious FHR readings.

Make a report stating all the causes/sources of the intermittent/spurious FHR readings and send the transducer assembled with the original cable to further second accredited lab testing for cable, and ultrasound beam profile as per Philips specifications to confirm the identified PZT disc/discs/components (including cable) being the source of spurious FHR response as outlined in the report. A list of all the probable sources of spurious FHR are listed below:

1. PZT discs—total number 7—loose, weak bonding to the plastic surface with air pockets and trapped loose adhesive particles intermittently produce very strong Doppler echo signals when they vibrate and get translated as spurious FHR anywhere from 60 bpm to 240 bpm.
2. Flat metal electrodes soldered to PZT discs to connect to the transmitter/receiver on front end PCB—total number 14—electrically and mechanically floating that contribute to spurious FHR.
3. Front-end PCB bonding to the plastic surface is weak resulting in sporadic/intermittent mechanical instability/movement that in turn makes the top-mounted backend PCB move intermittently directly in the path of the ultrasound beam resulting in Doppler Echo signal that is processed as spurious FHR (60 to 240 bpm).
4. Back-end PCB (Main CPU PCB) mounted on front-end PCB—mechanically unstable due to loose connectors to front-end PCB or the back-end PCB alone is loose due to no clamping force on it and it moves up-down relative to backend PCB intermittently causing spurious FHR.
5. Bottom Plastic Case has 3 threaded metal inserts—one or all three threaded metal inserts get loosened, allowing relative movement of top-bottom plastic cases and internal parts (models M2736A and M2736AA only, model ref #867246 do not have threaded metal inserts) which in turn cause spurious FHR.
6. Loose plastic spacer (battery housing used as a spacer) clamp. (Applicable to model ref #867246 only) that allows backend PCB movement intermittently resulting in spurious FHR.
7. Moisture intrusion due to loose top-bottom case, which causes multiple types of spurious and sometimes permanent failures after it gets condensed on SMD components' metallic leads which have spacing distances of 10-100 micro-meters.
8. Loose/rattling decoupling capacitors and other SMD (surface mount devices) components. Anything inside the transducer head that moves freely in the path of the ultrasound beam results in a Doppler signal and ultimately gets processed as spurious FHR between 60 to 240 bpm.
9. Excessive flux between electrical connections leads to SMD components, microcontroller, and all the active/passive components on the front-end as well as back-end PCB can lead to many types of intermittent failures, spurious FHR being one of them.
10. Front-end PCB connector crimp contacts corrode, resulting in intermittent open circuit, especially input to LVDS line receiver on back-end PCB. Open circuit inputs of the LVDS receiver pick up random noise that gets processed as spurious FHR between 60 to 240 bpm.
11. Cable connector assembly—an intermittent or permanent open circuit of conductors/input to LVDS—random noise is processed as spurious FHR from 60 to 240 BPM without transmission of ultrasound beam or in the absence of any ultrasound echo signal.
12. Cable connector assembly—direct permanent or intermittent shorting or resistive contact shorting of conductors, especially one of the LVDS input conductors to other conductors carrying signals CAN+, CAN− and Transducer Recognition.

Repaired, reworked, refurbished, and remanufactured transducer units—identify non-OEM/non-compliant parts and materials such as PZT discs, cable, adhesive bonding layer material, plastic top-bottom cases, rubber seal, etc. After-market replacement/non-OEM low-cost PZT discs' specifications variation tolerance is extremely high, +/−20% is very common and at times in the range of +/−80% or more. The center resonance frequency tolerance required for accurate FHR reading is +/−0.1% (as per Philips device specifications in manuals) and hence wrong FHR reading is very common with re-worked/refurbished/re-manufactured transducer units with non-Philips PZT discs and other parts. Most third-party replacement cable-connector assembly parts do not use balanced twisted pair conductors or comply with original specifications for the characteristic impedance for the reference signal transmission and hence pick up random noise that results in spurious FHR readings even though those conductors are physically intact as opposed to original Philips make a cable that starts being a source of spurious FHR problem only when conductors have intermittent or permanent electrical continuity (open circuit) problem.

Repaired, reworked, refurbished, and remanufactured transducer units should be checked to identify if there are any electrical circuit modifications on the front-end and back-end PCB.

The aforementioned testing procedure to pinpoint all sources of spurious FHR reading is extremely important for all Philips, Corometrics, Spacelabs, or any other manufacturer's fetal ultrasound transducer (irrespective of the model number) as there is no established procedure available in any of the relevant user/service manuals. In the worst-case scenario, it would take about 48 hours, but in most cases, the average time taken would be between 12 to 24 hours to confirm whether the ultrasound transducer unit has an intermittent/spurious FHR reading problem with root cause/causes identification which is very critical to know when a clinical fatality incidence is reported. There can be various situations such as an expectant mom is being monitored for twins, one of the ultrasound transducers has intermittent/spurious FHR detection issues but not being noticed by the clinical end user as the FHR sound set to be heard is from the other perfectly working transducer and the 'bad' transducer (with intermittent/spurious FHR issue) completely misses to sound an alarm that the fetus (one of the twins) is under stress. The 'bad' transducer is tested after the clinical incidence reporting by certified trained or authorized technical personnel from the manufacturer, adhering to the current procedure as per the equipment manuals, and may behave perfectly well as the cable flexing restores connections of LVDS inputs to normal when it is removed from the pregnant patient. Such a transducer with intermittent/spurious FHR problems would always be detected when tested following the procedure described in the previous section.

This testing procedure also serves as a set of qualitative and quantitative tests after any kind of service is performed that involves disassembly of the transducer head, replacement of components including PZT discs, cable, plastic cases, and re-bonding/adhesive gluing of PCB/PZT discs to the plastic substrate (bottom cases).

Figure 9:
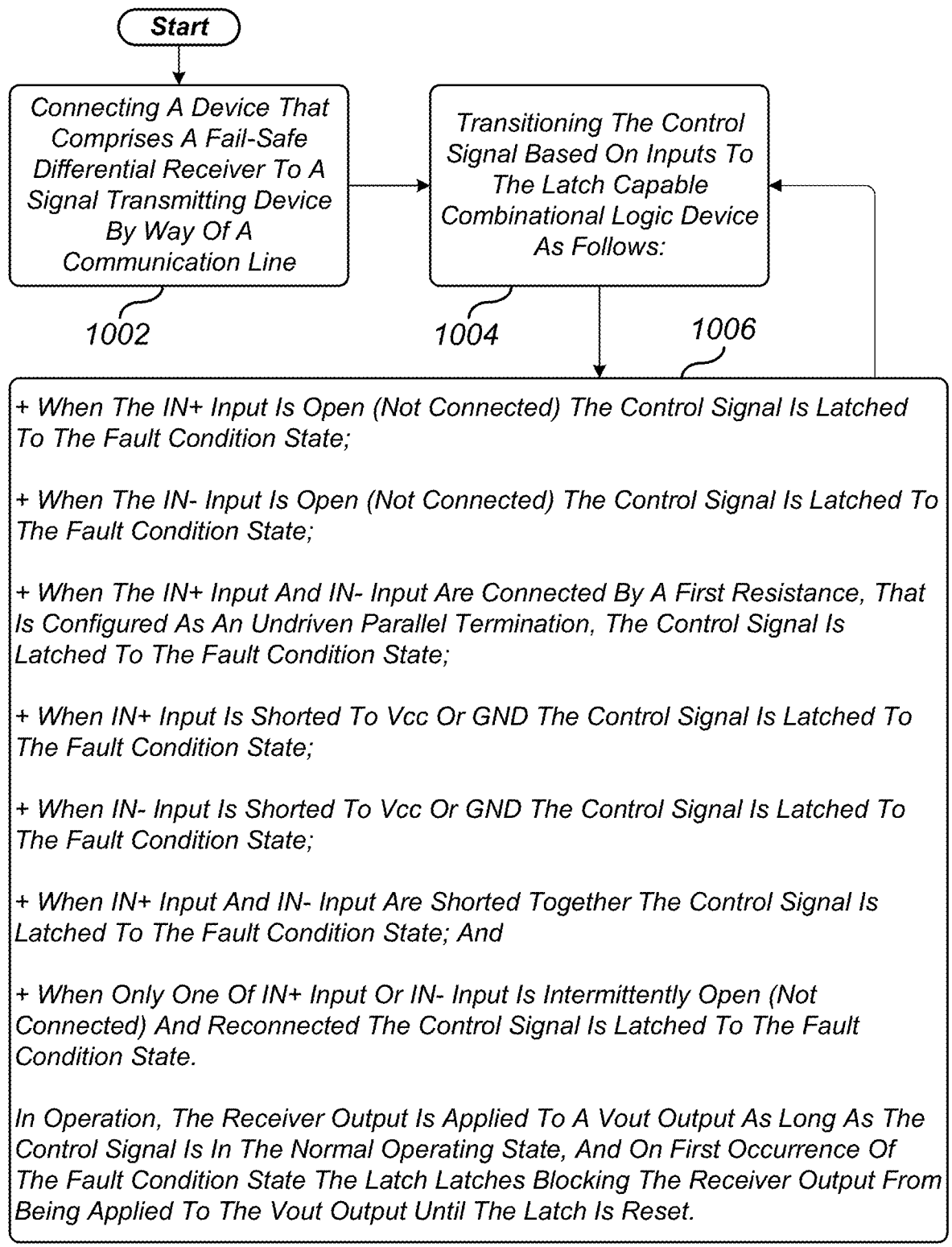
FIG. 9 illustrates one example of a method of using a fail-safe differential receiver having single differential input disconnect detection with a latchable control signal interrupt capability.

Referring to FIG. 9, there is illustrated one example of a method of using a fail-safe differential receiver 100 having single differential input disconnect detection with a latchable control signal interrupt capability. The method begins in step 1002.

In step 1002, a device that comprises a fail-safe differential receiver 100 is connected to a signal-transmitting device such as an FHR monitor 302 or other signal-transmitting devices by way of a communication line 330. The communication line comprises a plurality of electrical connections that include an IN+ 127, an IN− 129, Vcc, and ground (GND). The fail-safe differential receiver 100 is configured in one of the following ways:

Either the fail-safe differential receiver comprises a first voltage reference 131, a second voltage reference 132, a differential amplifier 111 that comprises a receiver output 143 and receives an IN+ input 127, and an IN− input 129, more than one of a comparator 108/112/114/116, each of the comparator 108/112/114/118 comprise a compared output and receive at least two of the following: the IN+ input 127, the IN− input 129, the first voltage reference 131, or the second voltage reference 132, and a latch-capable combinational logic device 179 that receives each of the compared output, and the receiver output 142, the latch-capable combinational logic device comprises a latch 122, and a control signal 133.

Or, the fail-safe differential receiver 100 comprises the first voltage reference 131, the second voltage reference 132, the differential amplifier 111 comprises the receiver output 143 and receives the IN+ input 127, and the IN− input 129, a first voltage follower operational amplifier 113 comprises a first op-amp output and receives the receiver output 143, a rectifier peak detector 115 comprises a peak output and receives the first op-amp output, a second voltage follower operational amplifier 117 comprises a second op-amp output and receives the peak output, a window comparator 119 comprises a window compared output and receives the second op-amp output. The fail-safe differential receiver 100 further comprises a first reference voltage 131, a second reference voltage 132, and the latch-capable combinational logic device 179 receives the window compared output and the receiver output 143. The latch-capable combinational logic device 129 comprises a latch 122, and the control signal 133.

In step 1004, the method then continues by transitioning the control signal 133 based on inputs to the latch-capable combinational logic device 179, the control signal 133 is switched to a normal operating state until at least one of the following is detected illustrated in block 1006:

when the IN+ 127 input is open (not connected) the control signal is latched to the fault condition state;

when the IN− 129 input is open (not connected) the control signal is latched to the fault condition state;

when the IN+ 127 input and the IN− 129 input are connected by a first resistance, that is configured as an undriven parallel termination, the control signal is latched to the fault condition state;

when the IN+ 127 input is shorted to Vcc or GND the control signal is latched to the fault condition state;

when the IN− 129 input is shorted to Vcc or GND the control signal is latched to the fault condition state;

when the IN+ 127 input and the IN− 129 input are shorted together the control signal is latched to the fault condition state; and when only one of the IN+ 127 input or the IN− 129 input is intermittently open and reconnected the control signal is latched to the fault condition state.

In operation, the receiver output 143 is applied to a Vout 180 output as long as the control signal 133 is in the normal operating state, and on the first occurrence of the fault condition state 420, the latch 122 latches blocking the receiver output 143 until the latch 122 is reset. The method returns to step 1004.

Figure 10:
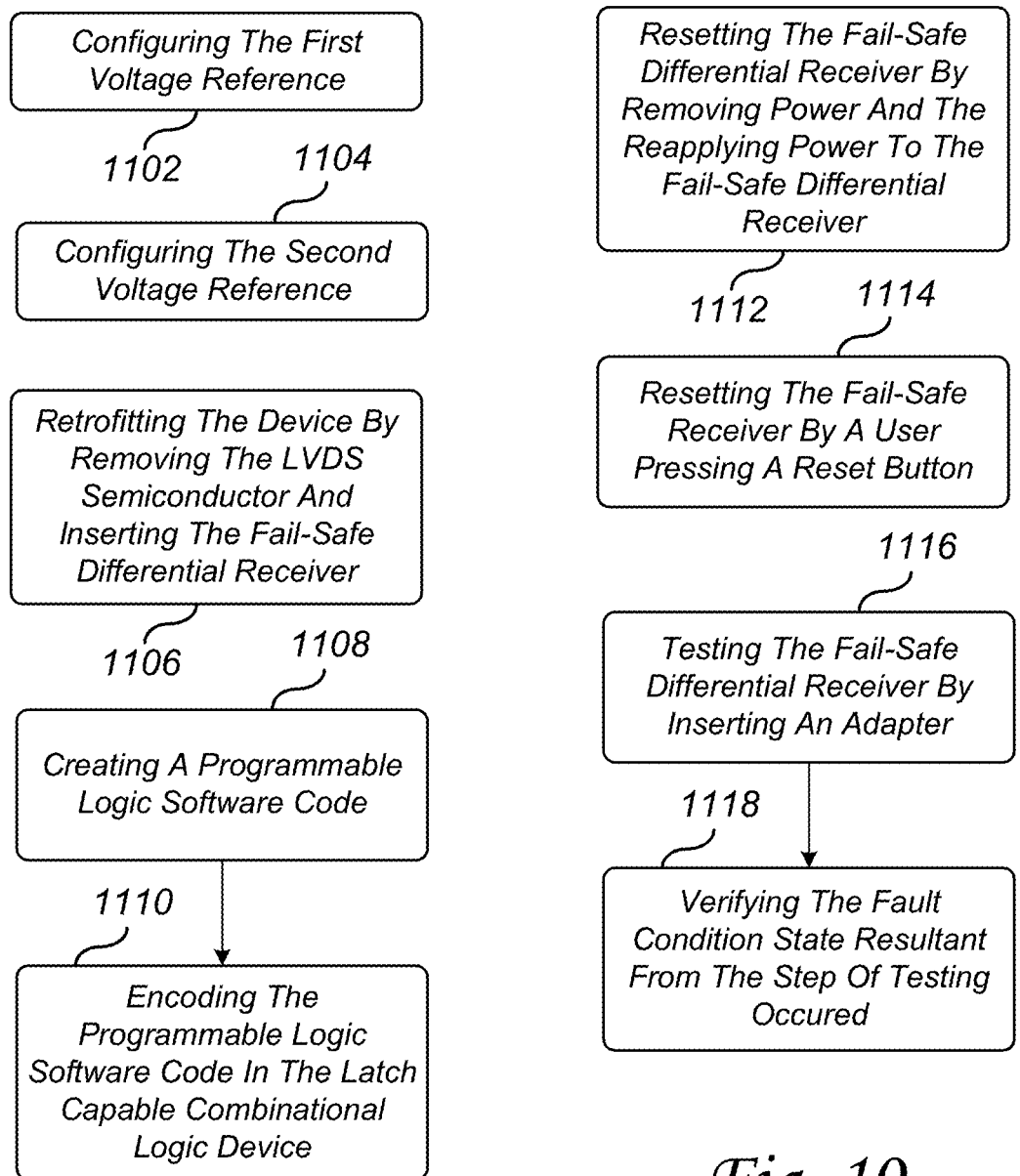
FIG. 10 illustrates exemplary embodiments that can be used interchangeably with the methods of the present invention.

Referring to FIG. 10, there are illustrated exemplary embodiments that can be used interchangeably with the methods of the present invention.

In step 1102, the first voltage reference 131 is configured. The first voltage reference 131 comprises a first resistor 132 connected in series with a second resistor 134 creating the first voltage reference 131 at the junction of the first resistor 132 and the second resistor 134. The first resistor 132 connects at one end to Vcc and the second resistor 134 connects at one end to GND. Values of the first resistor 132 and the second resistor 134 are selected such that the first voltage reference 131 is in the range of 97% of Vcc in the configuration illustrated in FIG. 3. For the configuration illustrated in FIG. 6, the first voltage reference Vref1 131 is in the range of Vop 149 plus the expected millivolts variation in normal operation plus 20 to 60 millivolt margin for the comparator to swing output from 0V to Vcc when a fault condition occurs.

In step 1104, the second voltage reference 132 comprises a third resistor 136 connected in series with a fourth resistor 138 creating the second voltage reference 132 at the junction of the third resistor 136 and the fourth resistor 138. The third resistor 136 connects at one end to Vcc and the fourth resistor 138 connects at one end to GND, values of the third resistor 136 and the fourth resistor 138 are selected such that the second voltage reference 132 is in the range of 0.03% of Vcc for the configuration illustrated in FIG. 3. For the configuration illustrated in FIG. 6, the second reference voltage Vre21 132 is in the range of Vop 149 minus the expected millivolts variation in normal operation minus 20 to 60 millivolts margin for the comparator to swing output from 0V to Vcc when a fault condition occurs.

In step 1106, the device can be retrofitted by removing the current LVDS semiconductor and inserting the fail-safe differential receiver 100. In this regard, the device can be an FHR transducer 336 or other suitable devices that comprises a prior LVDS. In this regard, the prior LVDS can be removed with a soldering iron or other suitable methods and the fail-safe differential receiver 100 of the present invention can be inserted in the place of the prior LVDS. Such fail-safe differential receiver 100 of the present invention can be a semiconductor for semiconductor swap of the fail-safe differential receiver 100 can be a small circuit card connected in place of the prior LVDS semiconductor. The small circuit card can be a combination of one or more semiconductors, resistors, diodes, capacitors, or other components as may be required and/or desired in a particular embodiment.

In an exemplary embodiment, a device such as a transducer 336 can be retrofitted by removing the current LVDS semiconductor and inserting the fail-safe differential receiver 100 of the present invention.

In step 1108, a programmable logic software code can be created. In this regard, programming languages such as VHDL, CUPL, and other suitable programming languages can be used to write logic software. The method then moves to step 1110.

In step 1110, the programmable logic software code can be encoded or otherwise downloaded into the latch-capable combinational logic device 179 causing the latch-capable combinational logic device 179 to operate in accordance with the step of transitioning the signal out in step 1004.

In step 1112, the fail-safe differential receiver 100 can be reset by removing power and then reapplying power to the fail-safe differential receiver 100.

In step 1114, the fail-safe differential receiver 100 can be reset by a user pressing a button or another system sending a reset logic signal to the fail-safe differential receiver 100.

In step 1116, the fail-safe differential receiver 100 is tested by inserting an adapter CON3 in series with the communication line 330 and pressing at least one of a button SW1/SW3 or switch SW2/SW4 to disconnect the IN+ input 127 or the IN− input 129. The adapter CON3 comprises the button SW1/SW3 or switch SW2/SW4. The method then moves to step 1118.

In step 1118, the fault condition state is verified resultant from the step of testing occurred.

In a plurality of exemplary embodiment, reference voltages Vref1 131 and Vref2 132 can be chosen to be close to Vop 149 (value of the normal function at differential amplifier 111) to speed up the fail-safe detection response. Additionally, many different resistance values 126/128/130/132/134/136/138/140/170/172 can be used, and the load or terminating resistor 130 is normally selected to match the impedance of the IN+ 127 and IN− 129 transmission lines, usually in the range of 50 to 120 ohms. The offset can be in the range of less than 50 mV, and a preferred range of 20 mV.

In an exemplary embodiment, various inversions in the logic can be introduced, and NAND gates rather than NOR gates can be substituted using DeMorgan's theorem. The inverting and non-inverting inputs to the comparators 108/112/114/118/146/148/150/152 and the differential amplifier 111 can be swapped to invert their outputs as may be required and/or desired in a particular embodiment. In addition, active logic low (L) signals rather than active logic high (H) signals can be substituted as may be required and/or desired in a particular embodiment. Furthermore, several logic gates can be combined into a larger gate, such as a 3 or 4 input AND or NAND gate as may be required and/or desired in a particular embodiment. The overall output can sometimes be disabled by turning 'OFF' the differential amplifier 111 with the fail-safe signal rather than blocking the receiver output 143 by way of the control signal 133 as may be required and/or desired in a particular embodiment.

In an exemplary embodiment, the reference voltage Vref2 132 near GND and the inputs to comparators 114/118 in FIG. 3 and comparator 152 in FIG. 6 can be swapped as may be required and/or desired in a particular embodiment.

In an exemplary embodiment, a flip-flop rather than an SR latch 122 may be substituted as may be required and/or desired in a particular embodiment. In addition, a toggle (T) or other kinds of latches or flip-flops can be substituted for the SR type latch 122 with appropriate logic changes for the latch 122 of flip-flop inputs. The RESET R input to latch 122 could be controlled by other systems or circuits as may be required and/or desired in a particular embodiment. Additional latches, buffers, and gates can be added as may be required and/or desired in a particular embodiment.

Figure 11:
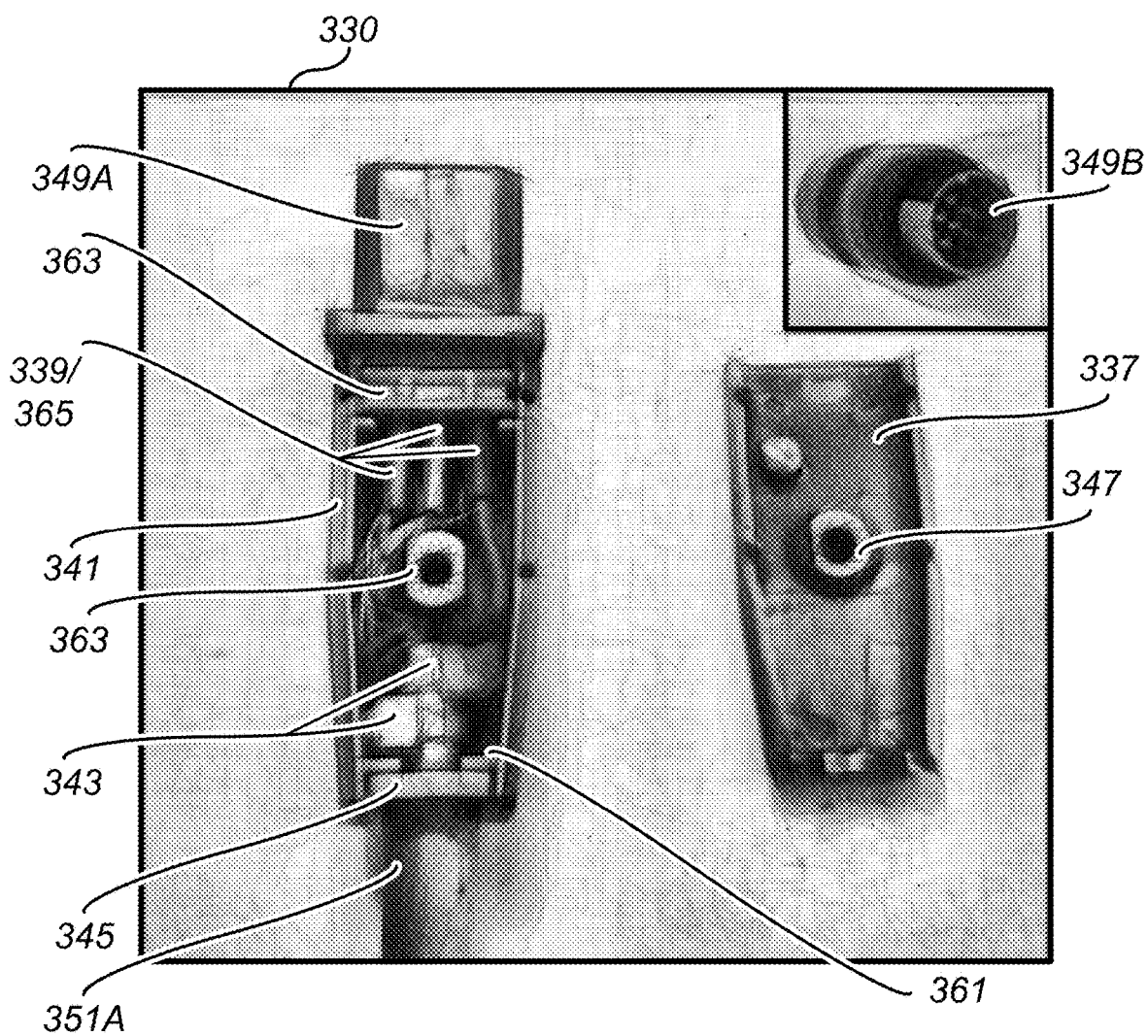
FIG. 11 illustrates one example of a cable assembly.
Figure 11:
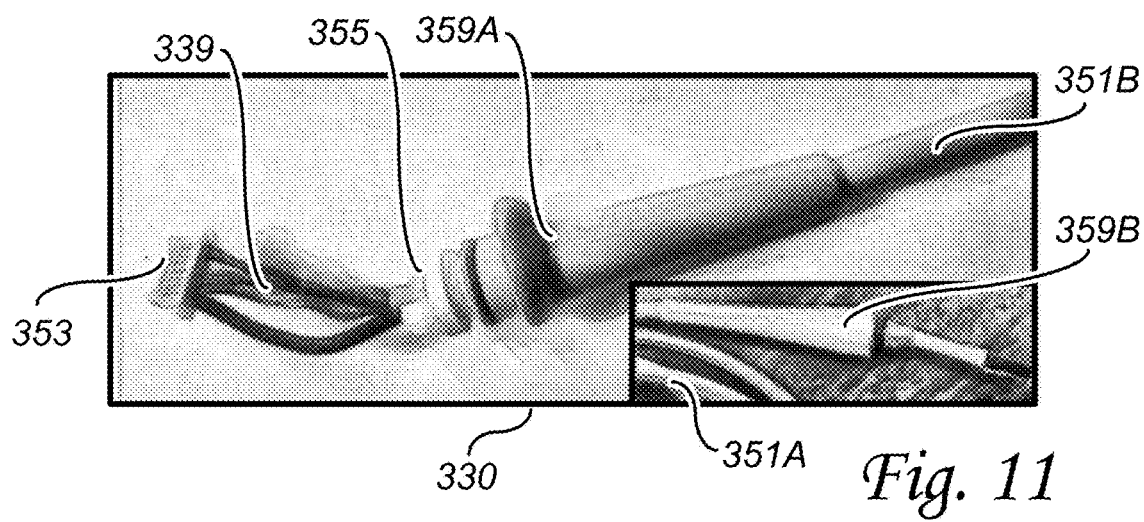

Referring to FIG. 11, there is illustrated one example of a cable 330 assembly. An advantage, in the present invention, is that, unlike prior cables that connect transducers 100 to fetal monitors 302 and notoriously fail where crimped and over-molded, the present invention, utilizes a fetal monitor end connector 349A/349B that has a hollow rigid body 341 made of plastic and a connector top 337 that can be manually fastened together by way of the screw hole 347 and standoff 363 formed within the hollow rigid body 341. Additionally, a strain relief 345 made out of 60 A shore hardness elastomer can be fitted into an integrally formed groove end 361 to secure cable 351 from pulling out of the hollow ridge body 340.

For disclosure purposes, fetal monitor end connectors 349A/349B are two different styles that interface to different models of fetal monitor 302. Other shaped types and kinds of fetal monitor end connectors 349 can be utilized as may be required and/or desired in a particular embodiment.

Additionally, the use of secondary strain relief 343 inside the hollow rigid body 341 further protects cable 351 against pulling forces and relieves stress on the individual conductors 339 that are crimped/soldered on contact pins 365 located at the wire connection end 363. In an exemplary embodiment, such secondary strain relief 343 can be at least two tie wraps or other suitable strain relief.

In an exemplary embodiment, electronic-grade silicone can be filled inside to make the connector compliant with IP68 specifications for water ingress. The increased length of the hollow rigid body 341 compared to the length of prior rubber over-molded approaches makes it easier for an operator to grab the hard-plastic connector for connecting and disconnecting from the fetal monitor 302.

In an exemplary embodiment, the transducer connector 353 terminates the individual conductors 339 on the opposite end of cable 351. The transducer connector 353 connects to the electronics inside the transducer 336 and strain relief 355 and rubber boot 359 secure the cable 351 inside the case of transducer 336.

In an exemplary embodiment, the transducer 336 can comprise cable 351 having a first cable end 351A and a second cable end 351B. A fetal monitor connector 349A/349B comprises a hollow rigid body 341 having a wire connection end 363 and an integrally formed groove end 361. A strain relief 345 is placed over the first cable end 351A and secured within the integrally formed grooved end 361 holding the first cable end 351A from slipping out of the hollow rigid body 341.

In an exemplary embodiment, a secondary strain relief 343 can be fastened around the first cable end 351A within the hollow rigid body 341 proximate to the strain relief 361.

In an exemplary embodiment, such secondary strain relief 343 can be at least two tie wraps fastened in parallel around the first cable end 351A within the hollow rigid body 341 proximate to the strain relief 361.

The secondary strain relief 343 further prevents the first cable end 351A from being pulled out of the hollow rigid body 341. More than one conductor 339 from the first cable end 351A terminates with electrical connections at the wire connection end 363. The fetal monitor connector 349A/349B plugs into a fetal monitor 302, and the second cable end 351B terminates with a transducer 336 connector 353.

In an exemplary embodiment, the hollow rigid body 341 can be filled with silicon, and a connector top 337 can be fastened by way of the screw hole 347 and standoff 363 to seal fetal monitor connector 349A/349B including the hollow rigid body 341.

In an alternative approach, the connector top 337 and standoff 363 can be eliminated, and fetal monitor connector 349A/349B including the hollow rigid body 341 can be filled and or otherwise sealed with silicon.

In an exemplary embodiment, the cable between the Philips Avalon ultrasound model M2736A, M2736AAA, Ref #867246 transducer head, and the fetal monitor is known to incur mechanical stress-related failures during the operation of monitoring the patient and over a period of time (based on usage). This can result in intermittent disconnection (open circuit) as well as intermittent noise pick-up due to characteristic impedance variation between a twisted pair of conductor wires.

An advantage in the present invention is that the fetal monitor end connector that is originally over-molded at the Philips factory during manufacture, is replaced with a hollow rigid body 341 with contact pin 365 as illustrated in FIG. 11 that can be manually assembled by hand. In this regard, the conductors 339 can be soldered to the contact pins 365 in place of crimping and two tie-wraps 343 can be used inside the hollow rigid body 341 to relieve the mechanical stress on the conductors 339. This approach eliminates associated problems due to over-molding at the connector end and maintains the characteristic impedance between the contact pins 365.

In the use of prior cables that use over-molding at the connector ends, during patient monitoring operation, the flexing of cable between the transducer head and the fetal monitor connector end can result in the physical separation of twisted pair conductors internally at various points along the length of cable that in turn cause spurious FHR readings by intermittent noise pick-up due to electrical unbalance. To overcome this unbalancing problem, in the present invention, a twisted pair of conductors (IN+ 127, IN− 129) for LVDS input connections can be tightly bunched together using fine cotton/nylon thread along the length and then wrapped in Teflon tape that will not allow physical separation in flexing operation. The insulation for these conductors is also changed to Teflon or any other tough elastomer from the original design of polypropylene to improve the mechanical toughness and withstand at least 10 million flexing cycle tests improving the durability of the cable.

In an exemplary embodiment, a cable 330, by way of more than one conductor 339, interconnects the IN+ input 127 and the IN− input 129 to a device such as FHR monitor 302. At least one end of the cable 330 terminates with more than one contact pin 365, a hollow rigid body 341, and a connector top 337.

During manufacture, manually by hand each conductor 339 is soldered to the contact pins 365 and secured within the hollow rigid body 341, and the connector top 337 is fastened to the hollow rigid body 341. Such fastening can be done by way of the screw hole 347 and standoff 363 using a screw or other suitable fastener. The contact pins 365 are secured within the hollow rigid body 341 in a manner that allows the contact pins 365 to extend outside the hollow rigid body 341 and interconnect with the device such as FHR monitor 302.

The capabilities of the present invention can be implemented in software, firmware, hardware, or some combination thereof.

As one example, one or more aspects of the present invention can be included in an article of manufacture (e.g., one or more computer program products) having, for instance, computer usable media. The media has embodied therein, for instance, computer readable program code means for providing and facilitating the capabilities of the present invention. The article of manufacture can be included as a part of a computer system or sold separately.

Additionally, at least one program storage device readable by a machine, tangibly embodying at least one program of instructions executable by the machine to perform the capabilities of the present invention can be provided.

The flow diagrams depicted herein are just examples. There may be many variations to these diagrams or the steps (or operations) described therein without departing from the spirit of the invention. For instance, the steps may be performed in a differing order, or steps may be added, deleted, or modified. All of these variations are considered a part of the claimed invention.

While the preferred embodiment of the invention has been described, it will be understood that those skilled in the art, both now and in the future, may make various improvements and enhancements which fall within the scope of the claims which follow. These claims should be construed to maintain the proper protection for the invention first described.

What is claimed is:

1. A fail-safe differential receiver having single differential input disconnect detection with latchable control signal interrupt capability comprising:
   a first voltage reference;
   a second voltage reference;
   a differential amplifier comprises a receiver output and receives an IN+ input, and an IN− input;
   more than one of a comparator, each of the comparator comprises a compared output and receive at least two of the following: the IN+ input, the IN− input, the first voltage reference, or the second voltage reference; and
   a latch-capable combinational logic device receives each of the compared output, and the receiver output, the latch-capable combinational logic device comprises a latch, and a control signal that is switched to a normal operating state until at least one of the following is detected:
      when the IN+ input is open (not connected) the control signal is latched to a fault condition state;
      when the IN− input is open (not connected) the control signal is latched to the fault condition state;
      when the IN+ input and the IN− input are connected by a first resistance, that is configured as an undriven parallel termination, the control signal is latched to the fault condition state;
      when the IN+ input is shorted to Vcc or GND the control signal is latched to the fault condition state;
      when the IN− input is shorted to Vcc or GND the control signal is latched to the fault condition state;
      when the IN+ input and the IN− input are shorted together the control signal is latched to the fault condition state; and
      when only one of the IN+ input or the IN− input is intermittently open and reconnected the control signal is latched to the fault condition state;
   wherein the receiver output is applied to a Vout output as long as the control signal is in the normal operating state, and on first occurrence of the fault condition state the latch latches blocking the receiver output from being applied to the Vout output until the latch is reset.

2. The fail-safe differential receiver in accordance with claim 1, the first voltage reference comprises a first resistor connected in series with a second resistor creating the first voltage reference at the junction of the first resistor and the second resistor, the first resistor connects at one end to Vcc and the second resistor connects at one end to GND.

3. The fail-safe differential receiver in accordance with claim 1, the second voltage reference comprises a third resistor connected in series with a fourth resistor creating the second voltage reference at the junction of the third resistor and the fourth resistor, the third resistor connects at one end to Vcc and the fourth resistor connects at one end to GND.

4. The fail-safe differential receiver in accordance with claim 1, the latch-capable combinational logic device comprises one or more of an OR gate, one or more of a NOR gate, one or more of an AND gate, one or more of a NAND gate, or one or more of an inverter.

5. The fail-safe differential receiver in accordance with claim 1, retrofitting a device by removing current LVDS semiconductor and inserting the fail-safe differential receiver.

6. The fail-safe differential receiver in accordance with claim 1, further comprising:
- a cable, by way of more than one of a conductor, interconnects the IN+ input and the IN− input to a device, at least one end of the cable terminates with more than one of a contact pin, a hollow rigid body, and a connector top;
- manually by hand each of the conductor is soldered to the contact pin and secured within the hollow rigid body, and the connector top is fastened to the hollow rigid body, the contact pins are secured within the hollow rigid body in manner that allows the contact pins to extend outside the hollow rigid body and interconnect with the device.

7. A fail-safe differential receiver having single differential input disconnect detection with latchable control signal interrupt capability comprising:
- a first voltage reference;
- a second voltage reference;
- a differential amplifier comprises a receiver output and receives an IN+ input, and an IN− input;
- a first voltage follower operational amplifier comprises a first op-amp output and receives the receiver output;
- a rectifier peak detector comprises a peak output and receives the first op-amp output;
- a second voltage follower operational amplifier comprises a second op-amp output and receives the peak output;
- a window comparator comprises a window compared output and receives the second op-amp output, a first reference voltage, and a second reference voltage;
- a latch-capable combinational logic device receives the window compared output and the receiver output, the latch-capable combinational logic device comprises a latch and a control signal that is switched to a normal operating state until at least one of the following is detected:
  - when the IN+ input is open (not connected) the control signal is latched to the fault condition state;
  - when the IN− input is open (not connected) the control signal is latched to the fault condition state;
  - when the IN+ input and IN− input are connected by a first resistance, that is configured as an undriven parallel termination, the control signal is latched to the fault condition state;
  - when the IN+ input is shorted to Vcc or GND the control signal is latched to the fault condition state;
  - when the IN− input is shorted to Vcc or GND the control signal is latched to the fault condition state;
  - when the IN+ input and the IN− input are shorted together the control signal is latched to the fault condition state; and
  - when only one of the IN+ input or the IN− input is intermittently open and reconnected the control signal is latched to the fault condition state;
- wherein the receiver output is applied to a Vout output as long as the control signal is in the normal operating state, and on first occurrence of the fault condition state the latch latches blocking the receiver output from being applied to the Vout output until the latch is reset.

8. The fail-safe differential receiver in accordance with claim 7, the latch-capable combinational logic device comprises one or more of an OR gate, one or more of a NOR gate, one or more of an AND gate, one or more of a NAND gate, or one or more of an inverter.

9. The fail-safe differential receiver in accordance with claim 7, the control signal is latched to the fault condition state when internal failure of the differential amplifier is detected by way of the second op-amp output switching to Vcc crossing either of the first voltage reference or the second voltage reference.

10. A fail-safe differential receiver having latchable control signal interrupt capability comprising:
- a differential amplifier comprises a receiver output and receives an IN+ input, and an IN− input;
- a first combining gate receives the receiver output, a control signal, and generates a Vout output;
- a first reference voltage;
- a first comparator receives the IN+ input and the first reference voltage, and generates a first compare signal;
- a second comparator receives the IN− input and the first reference voltage, and generates a second compare signal;
- a second combining gate receives the first compare signal and the second compare signal, and generates a third compare signal;
- a second reference voltage;
- a third comparator receives the IN+ input and the second reference voltage, and generates a fourth compare signal;
- a fourth comparator receives the IN− input and the second reference voltage, and generates a fifth compare signal;
- a third combining gate receives the fourth compare signal and the fifth compare signal, and generates a sixth compare signal;
- a fourth combining gate receives the third compare signal and the sixth compare signal, and generates a seventh compare signal; and
- a latch receives the seventh compare signal and generates the control signal, the control signal transitions between a normal operating state and a fault condition state;

wherein the receiver output is applied to the Vout output as long as the control signal is in the normal operating state, and on first occurrence of the fault condition state the latch latches blocking the receiver output from being applied to the Vout output until the latch is reset.

11. The fail-safe differential receiver in accordance with claim 10, the first voltage reference comprises a first resistor connected in series with a second resistor creating the first voltage reference at the junction of the first resistor and the second resistor, the first resistor connects at one end to Vcc and the second resistor connects at one end to ground (GND).

12. The fail-safe differential receiver in accordance with claim 10, the second voltage reference comprises a third resistor connected in series with a fourth resistor creating the second voltage reference at the junction of the third resistor and the fourth resistor, the third resistor connects at one end to Vcc and the fourth resistor connects at one end to ground (GND).

13. The fail-safe differential receiver in accordance with claim 10, the first combining gate is a OR gate, the second combining gate is a first NAND gate, the third combining gate is a second NAND gate, and the fourth combining gate is an OR gate.

14. The fail-safe differential receiver in accordance with claim 10, retrofitting a device by removing current LVDS semiconductor and inserting the fail-safe differential receiver.

15. A method of using a fail-safe differential receiver having single differential input disconnect detection with latchable control signal interrupt capability, the method comprising the steps of:
connecting a device that comprises a fail-safe differential receiver to a signal-transmitting device by way of a communication line, the communication line comprises a plurality of electrical connections that include an IN+ input, an IN− input, Vcc, and ground (GND), the fail-safe differential receiver is configured in one of the following ways:
either the fail-safe differential receiver comprises a first voltage reference, a second voltage reference, a differential amplifier comprises a receiver output and receives the IN+ input, and the IN− input, more than one of a comparator, each of the comparator comprises a compared output and receive at least two of the following: the IN+ input, the IN− input, the first voltage reference, or the second voltage reference, and a latch-capable combinational logic device receives each of the compared output, and the receiver output, the latch-capable combinational logic device comprises a latch, and a control signal; or
the fail-safe differential receiver comprises the first voltage reference, the second voltage reference, the differential amplifier comprises the receiver output and receives the IN+ input, and the IN− input, a first voltage follower operational amplifier comprises a first op-amp output and receives the receiver output, a rectifier peak detector comprises a peak output and receives the first op-amp output, a second voltage follower operational amplifier comprises a second op-amp output and receives the peak output, a window comparator comprises a window compared output and receives the second op-amp output, a first reference voltage, and a second reference voltage, the latch-capable combinational logic device receives the window compared output and the receiver output, the latch-capable combinational logic device comprises a latch, and the control signal;
transitioning the control signal based on inputs to the latch-capable combinational logic device, the control signal is switched to a normal operating state until at least one of the following is detected:
when the IN+ input is open (not connected) the control signal is latched to the fault condition state;
when the IN− input is open (not connected) the control signal is latched to the fault condition state;
when the IN+ input and the IN− input are connected by a first resistance, that is configured as an undriven parallel termination, the control signal is latched to the fault condition state;
when the IN+ input is shorted to Vcc or GND the control signal is latched to the fault condition state;
when the IN− input is shorted to Vcc or GND the control signal is latched to the fault condition state;
when the IN+ input and the IN− input are shorted together the control signal is latched to the fault condition state; and
when only one of the IN+ input or the IN− input is intermittently open and reconnected the control signal is latched to the fault condition state;
wherein the receiver output is applied to a Vout output as long as the control signal is in the normal operating state, and on first occurrence of the fault condition state the latch latches blocking the receiver output from being applied to the Vout output until the latch is reset.

16. The method in accordance with claim 15, further comprising:
configuring the first voltage reference, the first voltage reference comprises a first resistor connected in series with a second resistor creating the first voltage reference at the junction of the first resistor and the second resistor, the first resistor connects at one end to Vcc and the second resistor connects at one end to GND.

17. The method accordance with claim 15, the second voltage reference comprises a third resistor connected in series with a fourth resistor creating the second voltage reference at the junction of the third resistor and the fourth resistor, the third resistor connects at one end to Vcc and the fourth resistor connects at one end to GND.

18. The method in accordance with claim 15, further comprising:
retrofitting the device by removing current LVDS semiconductor and inserting the fail-safe differential receiver.

19. The method in accordance with claim 15, further comprising:
creating a programmable logic software code; and
encoding the programmable logic software code in the latch-capable combinational logic device causing the latch-capable combinational logic device to operate in accordance with the step of transitioning the control signal.

20. The method in accordance with claim 15, further comprising:
resetting the fail-safe differential receiver by removing power and then reapplying power to the fail-safe differential receiver.

21. The method in accordance with claim 15, further comprising:
testing the fail-safe differential receiver by inserting an adapter in series with the communication line and pressing at least one of a button or switch to disconnect the IN+ input or the IN− input, the adapter comprises the button or switch; and
verifying the fault condition state resultant from the step of testing occurred.

* * * * *